(12) United States Patent
Ueda et al.

(10) Patent No.: US 8,679,425 B2
(45) Date of Patent: Mar. 25, 2014

(54) REAGENT CONTAINER AND REAGENT SET

(75) Inventors: Sachiko Ueda, Hyogo (JP); Yusuke Mori, Kobe (JP); Hiroyuki Ohashi, Kobe (JP); Yuji Itose, Hyogo (JP); Kinya Uchihashi, Kakogawa (JP); Yoichi Nakamura, Kobe (JP); Kohei Sugitani, Kobe (JP)

(73) Assignee: Sysmex Corporation, Kobe (JP)

(*) Notice: Subject to any disclaimer, the term of this patent is extended or adjusted under 35 U.S.C. 154(b) by 507 days.

(21) Appl. No.: 12/837,869

(22) Filed: Jul. 16, 2010

(65) Prior Publication Data
US 2011/0014095 A1 Jan. 20, 2011

(30) Foreign Application Priority Data
Jul. 16, 2009 (JP) .................... 2009-167718
Feb. 2, 2010 (JP) .................... 2010-021570

(51) Int. Cl.
*B01L 3/00* (2006.01)
*B01L 9/00* (2006.01)
*B01L 99/00* (2010.01)
*B65D 21/02* (2006.01)
*B65D 1/24* (2006.01)
*B65D 25/04* (2006.01)
*B65D 57/00* (2006.01)
*B65D 85/00* (2006.01)
*G01N 21/00* (2006.01)
*G01N 31/00* (2006.01)
*G01N 33/00* (2006.01)
*A47B 77/00* (2006.01)
*B65D 6/28* (2006.01)

(52) U.S. Cl.
USPC ............ 422/547; 422/64; 422/65; 422/556; 422/560; 422/569; 220/4.01; 220/23.2; 220/500; 312/107

(58) Field of Classification Search
USPC ............ 422/64, 521, 549; 220/23.2, 234, 500
See application file for complete search history.

(56) References Cited

U.S. PATENT DOCUMENTS

| | | | |
|---|---|---|---|
| 4,938,369 A * | 7/1990 | Carilli ........................ 211/74 |
| 5,665,315 A | 9/1997 | Robert et al. |
| 2003/0070498 A1 | 4/2003 | Ohyama et al. |
| 2009/0142844 A1* | 6/2009 | Le Comte ................... 436/8 |
| 2010/0243103 A1 | 9/2010 | Ono et al. |

FOREIGN PATENT DOCUMENTS

| | | |
|---|---|---|
| CA | 2132813 A1 | 4/1995 |
| JP | 39-035529 U | 11/1964 |
| JP | 02-087727 U | 7/1990 |
| JP | 05-016110 Y2 | 4/1993 |
| JP | 07-191039 A | 7/1995 |

(Continued)

*Primary Examiner* — Jill Warden
*Assistant Examiner* — Julie Tavares
(74) *Attorney, Agent, or Firm* — Brinks Gilson & Lione

(57) ABSTRACT

A reagent container set is disclosed which comprises: a first reagent container for accommodating a first reagent to be used in a sample analyzer, the top part of the first reagent container having a first aspiration opening for inserting a first reagent aspirating tube to aspirate the first reagent; a waste fluid container for accommodating the first reagent used in the sample analyzer as a waste fluid, the top of the waste fluid container having a discharge opening for inserting a waste fluid discharging tube to discharge the waste fluid into the waste fluid container; a box for accommodating the first reagent container and the waste fluid container; and a container holding member for holding the first reagent container and the waste fluid container so that the first aspiration opening and the discharge opening are disposed at predetermined positions, the container holding member being maintained at a predetermined position within the box.

29 Claims, 29 Drawing Sheets

(56) References Cited

FOREIGN PATENT DOCUMENTS

| | | |
|---|---|---|
| JP | 08-105900 A | 4/1996 |
| JP | 10-129670 A | 5/1998 |
| JP | 2002-205730 A | 7/2002 |
| JP | 2003-083983 A | 3/2003 |
| JP | 2004163319 A * | 6/2004 |
| JP | 2008-074458 A | 4/2008 |
| JP | 2008-132232 A | 6/2008 |
| JP | 2009-113851 A | 5/2009 |
| JP | 2009-149310 A | 7/2009 |
| WO | WO 2007006903 A2 * | 1/2007 |
| WO | WO 2008003338 A1 * | 1/2008 |

* cited by examiner

REAGENT CONTAINER AND REAGENT SET

RELATED APPLICATIONS

This application claims priority under 35 U.S.C. §119 to Japanese Patent Application Nos. 2009-167718 filed on Jul. 16, 2009 and 2010-021570 filed on Feb. 2, 2010, the entire content of which is hereby incorporated by reference.

FIELD OF THE INVENTION

The present invention relates to a reagent container set and reagent set, and specifically relates to a reagent container set and reagent set provided with a reagent holding container and waste container.

BACKGROUND OF THE INVENTION

There are known conventional reagent containers and reagent sets provided with a reagent holding container and waste container (for example, refer to Japanese Utility Model publication 5-16110).

Japanese Utility Model publication 5-16110 discloses a stock fluid and waste fluid exchange container provided with a stock fluid bag for holding a stock fluid and having an opening at the top of the bag for the insertion of a tube for aspirating a stock fluid, a waste fluid bag for collecting, as waste fluid, the stock fluid that has been used in a stock fluid using device and having an opening at the top of the bag for the insertion of a tube for discharging the waste fluid, and an external box case with openings at positions corresponding to the opening of the stock fluid bag and the opening of the waste fluid bag such that the stock fluid bag and waste fluid bag are adjacent to each other. This exchange container is configured so that the stock fluid aspirating tube is inserted in the opening of the stock fluid bag and the opening corresponding to the external box case, and the waste fluid discharge tube is inserted in the opening of the waste fluid bag and the opening corresponding to the external box case.

However, the exchange container disclosed in Japanese Utility Model publication 5-16110 may experience dislocation of the stock fluid bag and the waste fluid bag from the predetermined positions arising from inclination and the like of the exchange container during transport or the like. In this case, handling is difficult since it becomes difficult to insert the stock fluid aspirating tube and the waste fluid discharge tube in the respective opening of the stock fluid bag and the opening of the waste fluid bag because the opening of the stock fluid bag and the opening of the waste fluid bag are dislocated relative to the respective openings of the external box case.

SUMMARY OF THE INVENTION

The scope of the present invention is defined solely by the appended claims, and is not affected to any degree by the statements within this summary.

The reagent container set of a first aspect of the present invention provides a reagent container set comprising:

a first reagent container for accommodating a first reagent to be used in a sample analyzer, the top part of the first reagent container having a first aspiration opening for inserting a first reagent aspirating tube to aspirate the first reagent;

a waste fluid container for accommodating the first reagent used in the sample analyzer as a waste fluid, the top of the waste fluid container having a discharge opening for inserting a waste fluid discharging tube to discharge the waste fluid into the waste fluid container;

a box for accommodating the first reagent container and the waste fluid container; and a container holding member for holding the first reagent container and the waste fluid container so that the first aspiration opening and the discharge opening are disposed at predetermined positions, the container holding member being maintained at a predetermined position within the box.

The reagent set of a second aspect of the present invention provides a reagent set comprising: the reagent container set having the structure described above; and the first reagent accommodated in the first reagent container.

The reagent container set of a third aspect of the present invention includes a reagent container set comprising:

a first reagent container for accommodating a first reagent to be used in a sample analyzer, the top part of the first reagent container having a first aspiration opening for inserting a first reagent aspirating tube to aspirate the first reagent;

a second reagent container for accommodating a second reagent to be used in the sample analyzer, the top part of the second reagent container having a second aspiration opening for inserting a second reagent aspirating tube to aspirate the second reagent, and the height of which is lower than the first reagent container;

a waste fluid container for accommodating the first reagent and the second reagent used in the sample analyzer as a waste fluid, the top of the waste fluid container having a discharge opening for inserting a waste fluid discharging tube to discharge the waste fluid;

a container support for supporting the bottom of the second reagent container so that the bottom of the second reagent container is positioned at a higher position than the bottom of the first reagent container; and a box for accommodating the first reagent container, second reagent container, waste fluid container, and container support.

The reagent container set of a fourth aspect of the present invention provides a reagent container set comprising:

a reagent container for accommodating a reagent to be used in a sample analyzer;

a waste fluid container for accommodating the reagent used in the sample analyzer as a waste fluid;

a container accommodating part for accommodating the reagent container and the waste fluid container, and which has a plurality of outer side surfaces, wherein:

the top of the waste fluid container comprises a discharge opening for discharging the waste fluid accommodated in the waste fluid container;

the waste fluid container is accommodated in the container accommodating part so that the discharge opening is disposed adjacent to the outer side of the container accommodating part; and the container accommodating part comprises a notch at the top end part of an outer side surface nearest the discharge opening so that the notch is opposite the discharge opening among the plurality of outer side surfaces of the container accommodating part.

The reagent container set of a fifth aspect of the present invention provides a reagent container set comprising:

a box body defining a first space inside thereof;

a first interior member placed in the box body to define a second space in the first space, the second space being no larger than the first apace;

a first and a second containers, in which a reagent and a reagent waste are storable respectively, configured to collectively substantially occupy the second space and generally immobilized in the second space, each container having a generally tubular opening in a top surface thereof; and two holding devices provided in the first interior member so as to be spaced apart at a distance between the tubular openings of the first and second containers and configured to generally hold the tubular openings relative to each other and to the box body.

DETAILED DESCRIPTION OF THE PREFERRED EMBODIMENT

The embodiments of the present invention are described hereinafter based on the drawings.

(First Embodiment)

The structure of the reagent set of a first embodiment of the present invention is described below with reference to FIGS. 1 through 18.

Figure 1:
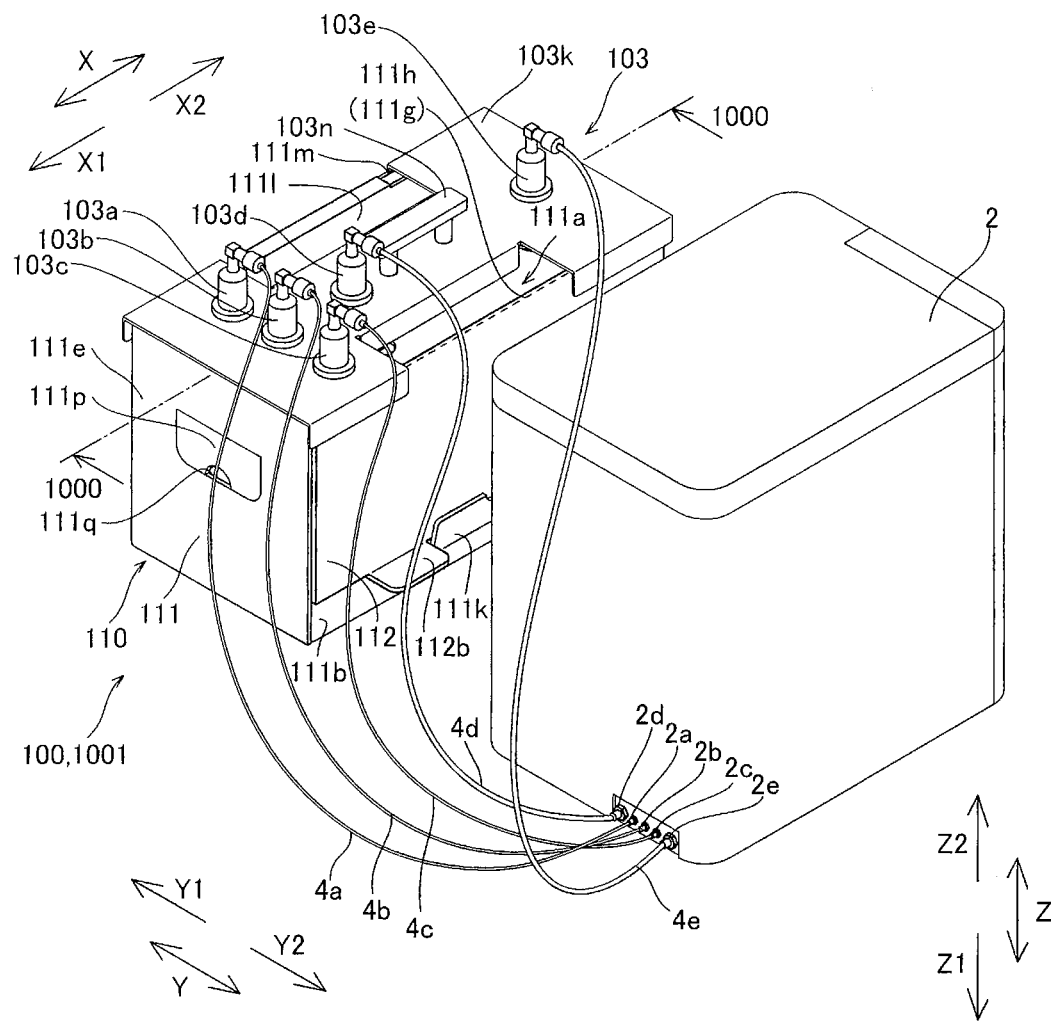
FIG. 1 is a perspective view showing the structure of the reagent removal member, sample analyzer, and reagent set of a first embodiment of the present invention.
Figure 5:
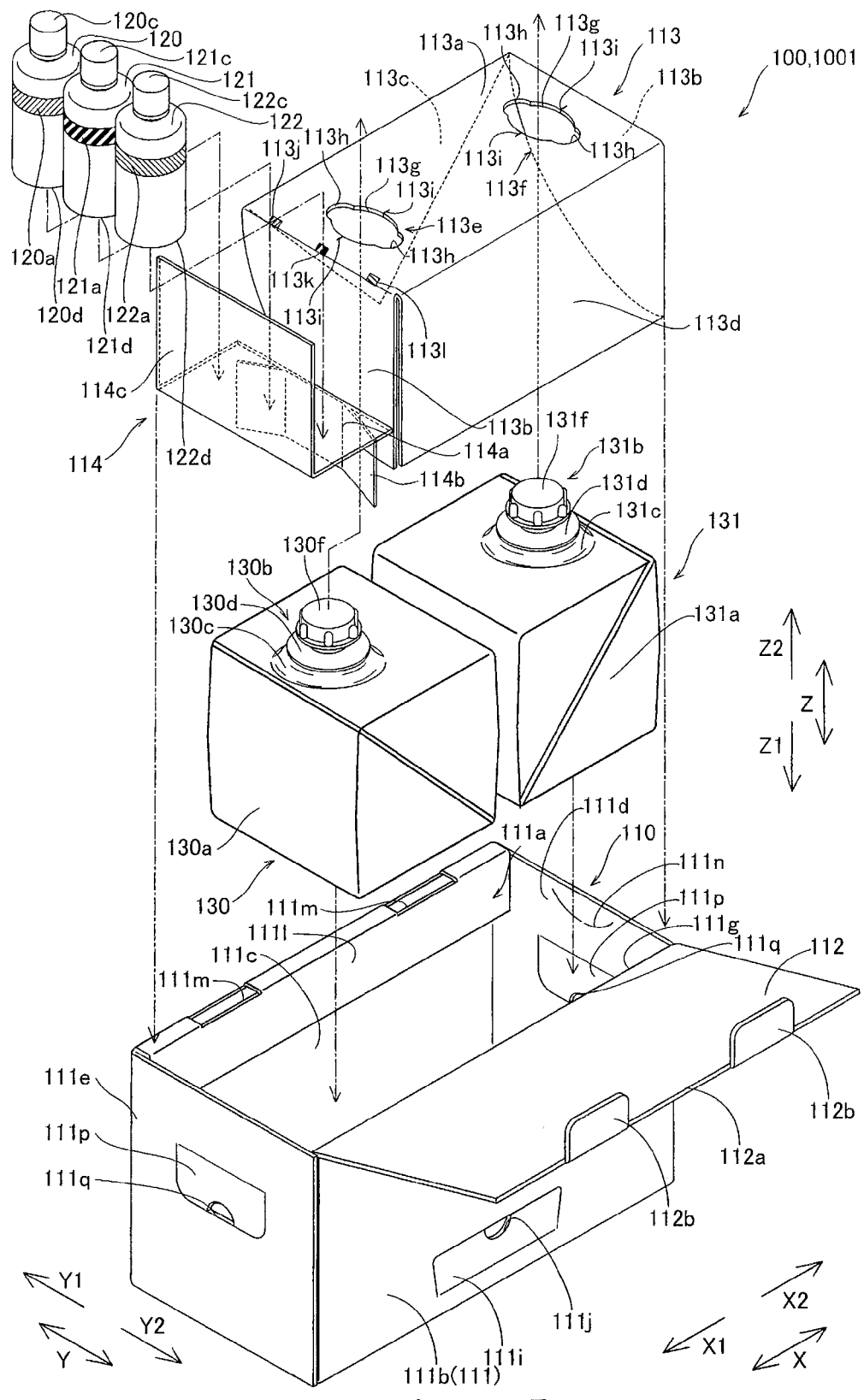
FIG. 5 is an exploded perspective view showing the general structure of the first embodiment of the reagent set of the present invention.

As shown in FIG. 1, the reagent set 100 of the first embodiment is connected to a sample analyzer 2 (a blood cell counter for counting blood cells in blood in the present embodiment) via a reagent extraction member 103 with a cover 112 (described later) of the reagent set 100 in an open state. The reagent set 100 includes a reagent container 1001, and reagent accommodated in each reagent storage container of the reagent container 1001. As shown in FIG. 5, the reagent container 1001 includes a hemolytic agent storage container 120 used for hemoglobin measurement, hemolytic agent storage container 121 used for white blood cell classification and measurement, staining agent storage container 122 used for reticulocyte measurement, diluting liquid container 130, waste fluid container 131, box 110 for housing these containers, container holding member 113 disposed in the arrow X2 direction within the box 110, and container supporting member 114 disposed in the arrow X1 direction within the box 110.

Figure 2:
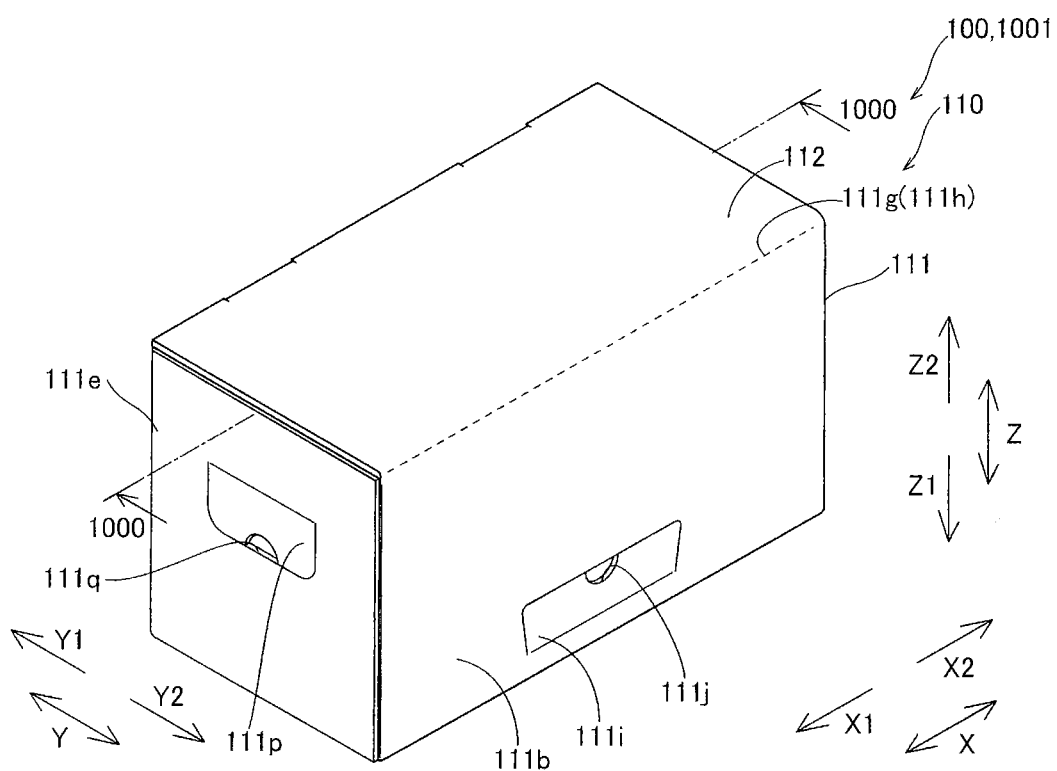
FIG. 2 is a perspective view showing the exterior of the first embodiment of the reagent set of the present invention when the cover is in a closed state.

The box 110 measures approximately 390 mm in the X direction, approximately 390 mm in the Y direction, and approximately 230 mm in the Z direction (exterior dimensions), as shown in FIG. 2. The box 110 includes a box body 111, and a cover 112 which is integratedly formed with the box body 111.

When the reagent set 100 is used, the hemolytic agent storage container 120 used for hemoglobin measurement, hemolytic agent storage container 121 used for white blood cell classification and measurement, staining agent storage container 122, diluting liquid container 130, and waste fluid container 131 are used without removal from the box 110.

Figure 4:
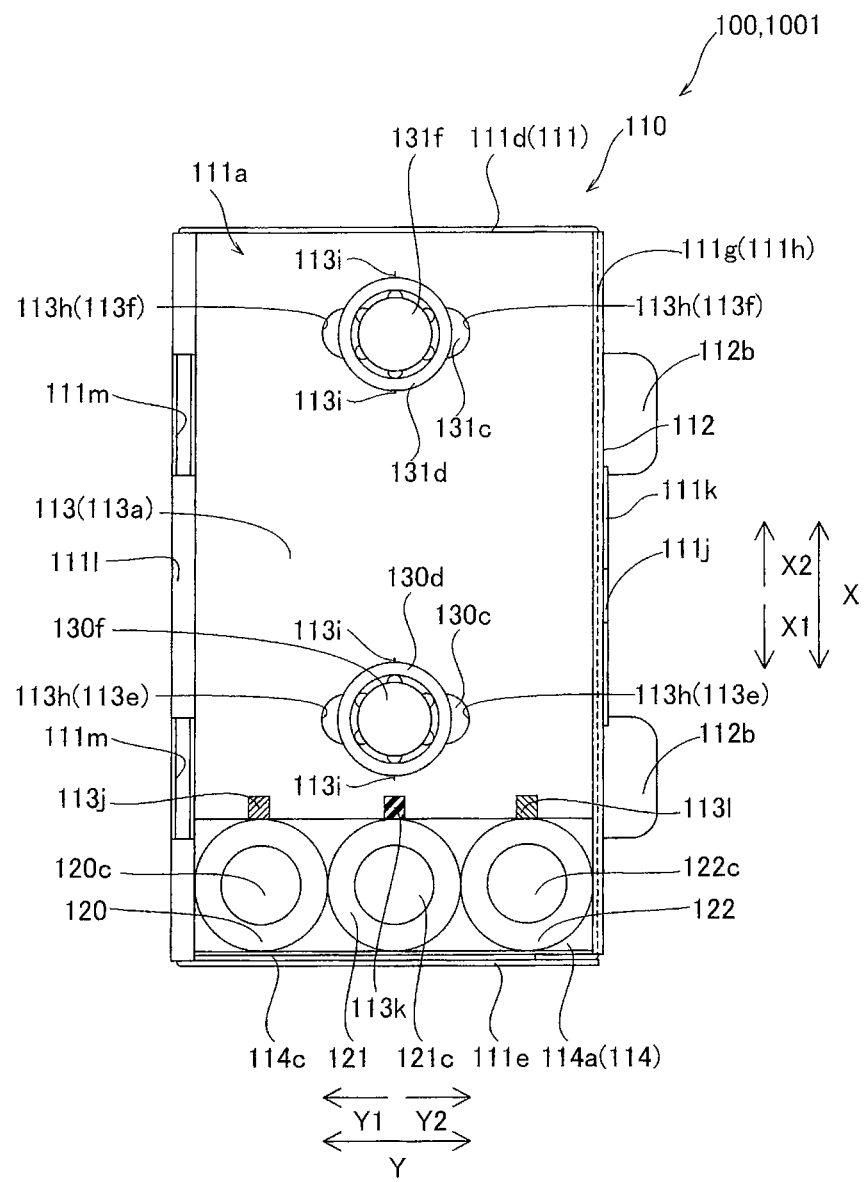
FIG. 4 is a top view showing the first embodiment of the reagent set of the present invention when the cover is in an open state.

The hemolytic agent storage container 120, hemolytic agent storage container 121, and staining agent storage container 122 are disposed on a support 114a (described later) of the container supporting member 114 on the arrow X1 direction side within the box body 111 (refer to FIGS. 4 through 6). The diluting liquid container 130 is disposed at the approximate center within the box body 111, and the waste fluid container 131 is disposed on the arrow X2 direction side within the box body 111. Thus, the diluting liquid container 130 is disposed in the X direction between the container support member 114 on the arrow X1 direction side, and the waste fluid container 131 on the arrow X2 direction side.

Figure 7:
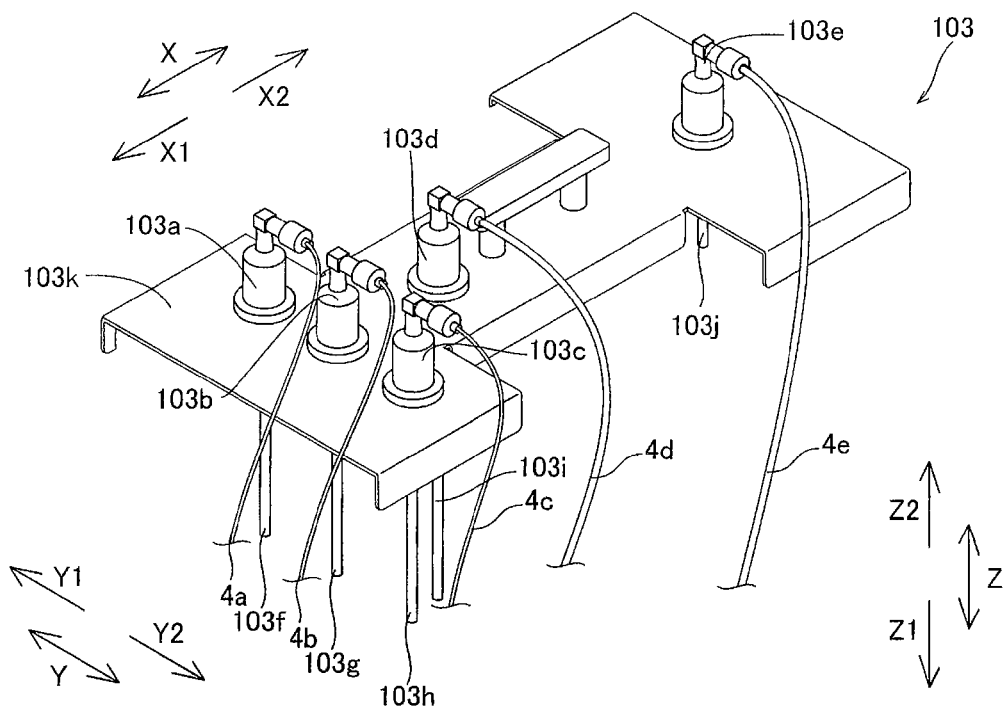
FIG. 7 is a perspective view showing the structure of the reagent removal member of the reagent set of a first embodiment of the present invention.

In addition, as shown in FIG. 1, during use of the reagent set 100, the reagent extraction member 103 is disposed so as to cover the opening 111a of the box body 111 from above (arrow Z2 direction side). As shown in FIG. 7, this reagent extraction member 103 has reagent extraction units 103a, 103b, 103c and 103d that correspond to the hemolytic agent storage container 120, hemolytic agent storage container 121, staining agent storage container 122, and diluting liquid container 130 (refer to FIG. 5). The extraction member 103 also has a waste fluid discharging unit 103e that corresponds to the waste fluid container 131 (refer to FIG. 5).

Figure 8:
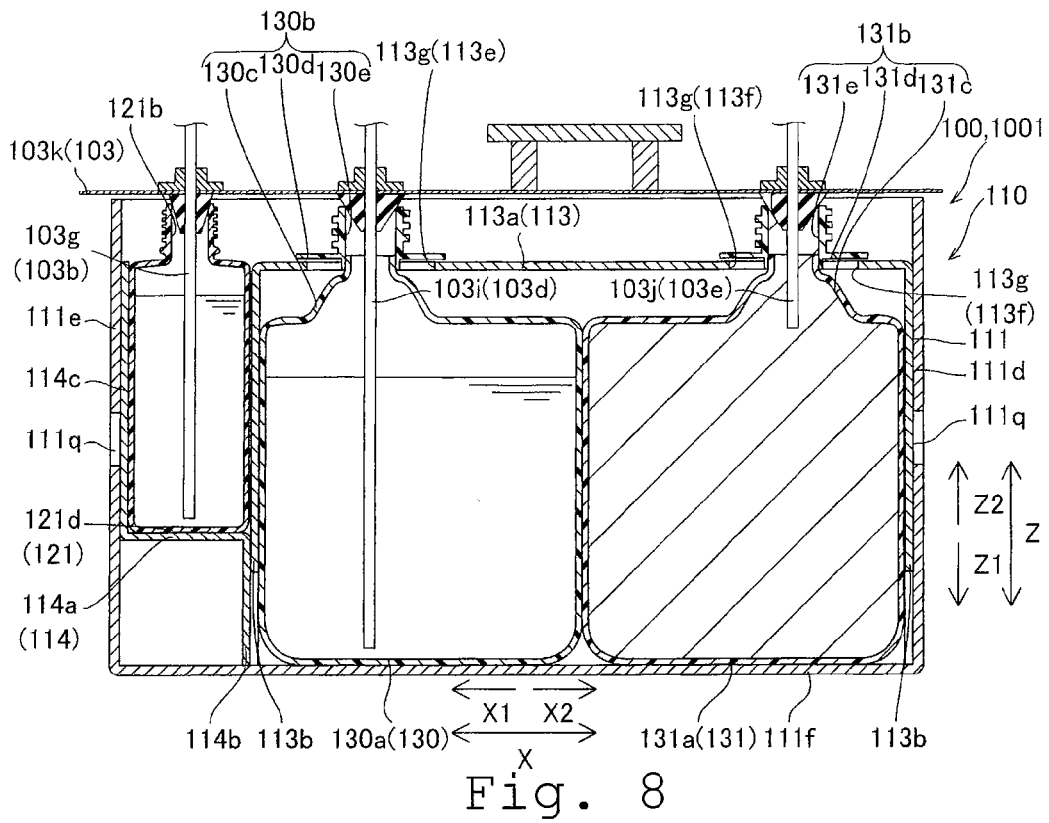
FIG. 8 is a cross sectional view along the 1000-1000 line of FIG. 1 showing the reagent removal member condition.

The reagent extraction units 103a, 103b, 103c, and 103d also include reagent aspirating tubes 103f, 103g, 103h, and 103i, respectively, for aspirating the reagents, and the waste fluid discharge unit 103e includes a waste fluid discharging tube 103j for discharging the waste fluid. As shown in FIGS. 7 and 8, the reagent extraction units 103a, 103b, 103c, 103d, and the waste fluid discharge unit 103e are fixedly attached to a metal plate 103k. Thus, the reagent aspirating tubes 103f, 103g, 103h, 103i, and the waste fluid discharging tube 103j are anchored and supported so as to not vary their mutual positions.

As shown in FIG. 1, the reagent extraction units 103a, 103b, 103c, 103d, and the waste fluid discharging unit 103e are connected to the inlets 2a, 2b, 2c, 2d, and outlet 2e through tubes 4a, 4b, 4c, 4d, and 4e, respectively, and are configured to be deployable in the box body 111 while maintaining the connected state.

Figure 9:
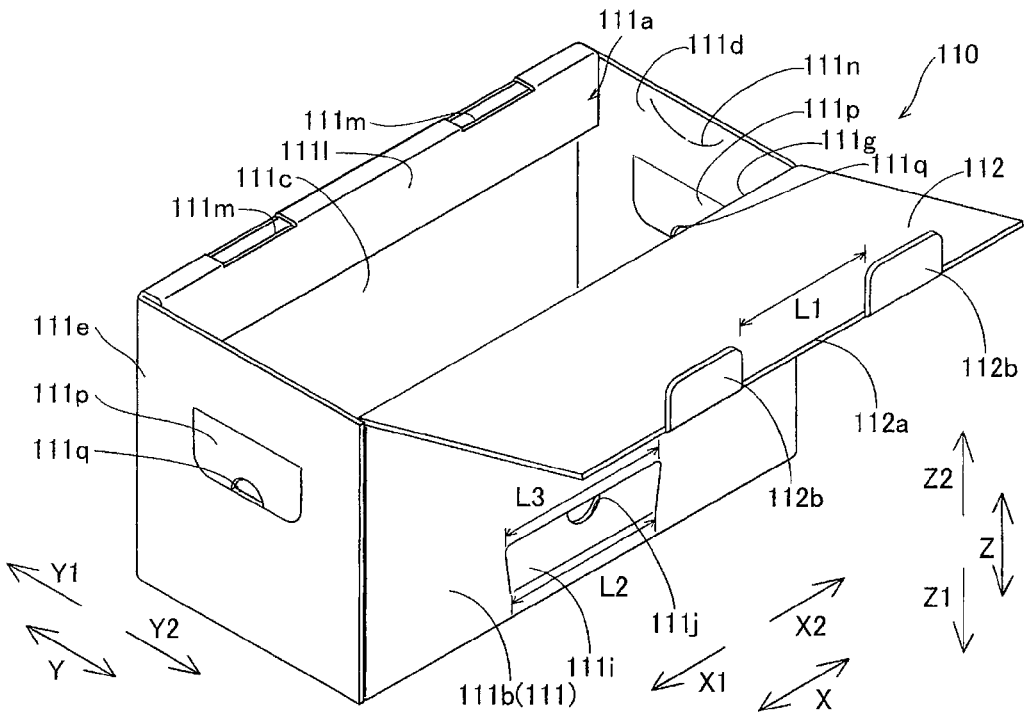
FIG. 9 is a perspective view showing the box of the first embodiment of the reagent set of the present invention.

As shown in FIG. 9, the box body 111 is configured by corrugated cardboard approximately 5 mm in thickness, and has an approximate rectangular shape. The box body 111 includes an opening 111a formed on the side in the arrow Z2 direction, side surface 111b formed on the side in the arrow Y2 direction, side surface 111c formed on the side in the arrow Y1 direction, side surface 111d formed on the side in the arrow X2 direction, side surface 111e formed on the side in the arrow X1 direction, and bottom surface 111f formed on the side in the arrow Z1 direction (refer to FIG. 6).

Figure 3:
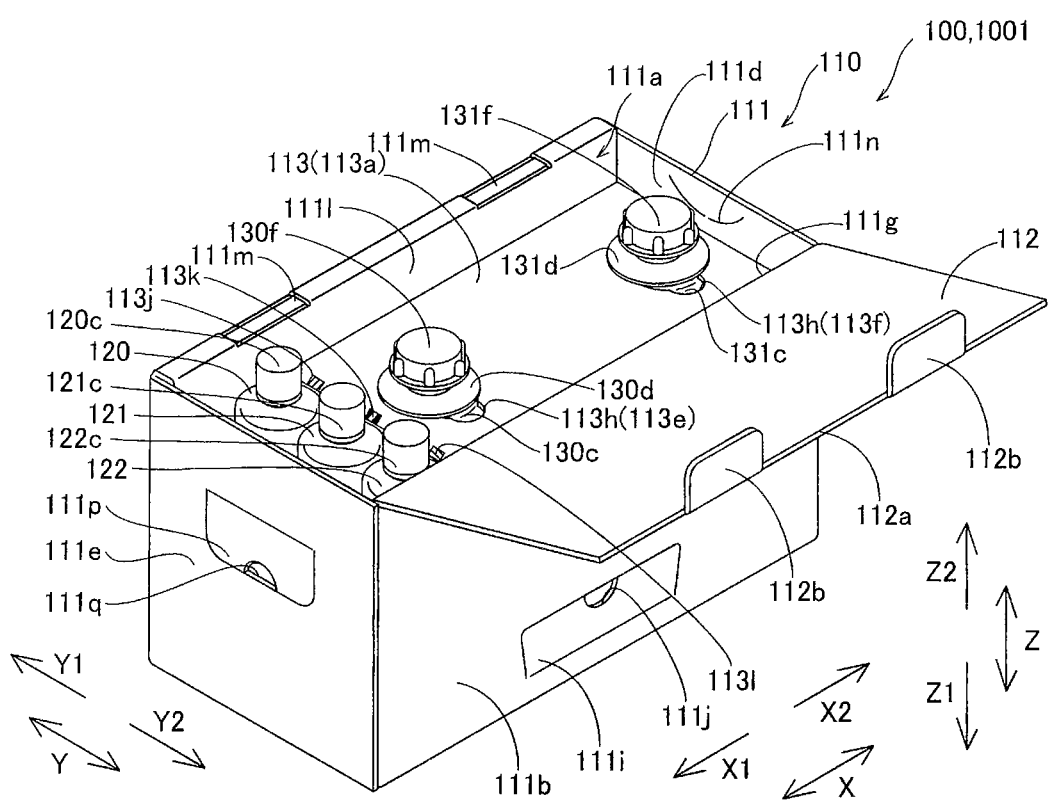
FIG. 3 is a perspective view showing the exterior of the first embodiment of the reagent set of the present invention when the cover is in an open state.

The top end of the side surface 111b (in the arrow Z2 direction) is provided with a connector 111g that is connected to the side surface 111b and the cover 112 that is integratedly formed with the box body 111. A corresponding cut 111h is formed on the inner side (the opening 111a side shown in FIG. 11) and the outer side (outer side shown in FIG. 2) of the connector 111g. Thus, the cover 112 is configured to be maintained in a somewhat open state via the cut 111h when the cover 12 has been opened from the position in which the cover 112 closes the opening 111a as shown in FIG. 2 so as to open the opening 111a as shown in FIG. 3. It is therefore possible to prevent the cover 112 from being positioned so as to again close the opening 111a.

Figure 10:
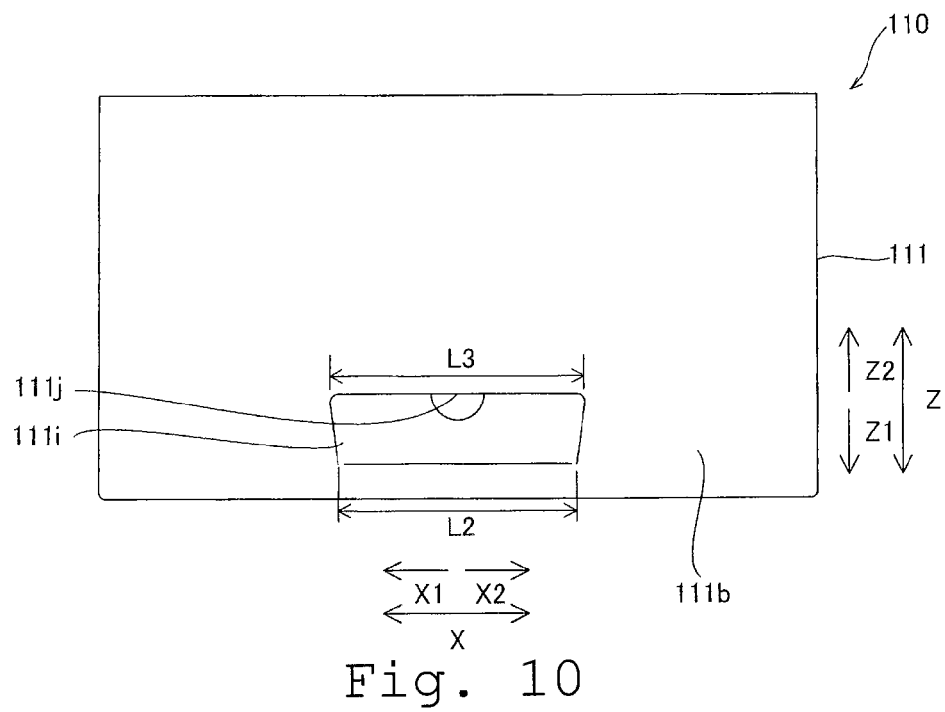
FIG. 10 is a side view showing the side surface of the cover side of the box of the first embodiment of the present invention.

The side surface 111b is also provided with a latch forming part 111i, as shown in FIG. 10. The latch forming part 111i is configured to be capable of pivoting on the bottom end (side in the arrow Z1 direction) so that the top end (side in the arrow Z2 direction) separates from the side surface 111b to the side in the arrow Y2 direction (refer to FIG. 11). The latch forming part 111i has an approximate trapezoidal shape in which the length in the X direction increases from the bottom end toward the top end. A hole 111j is formed in the approximate center in the X direction of the top end of the latch forming part 111i so that a user can insert a finger therein to separate the top end from the side surface 111b. Thus, the latch forming part 111i can be separated to form a latch 111k (refer to FIG. 11).

Figure 11:
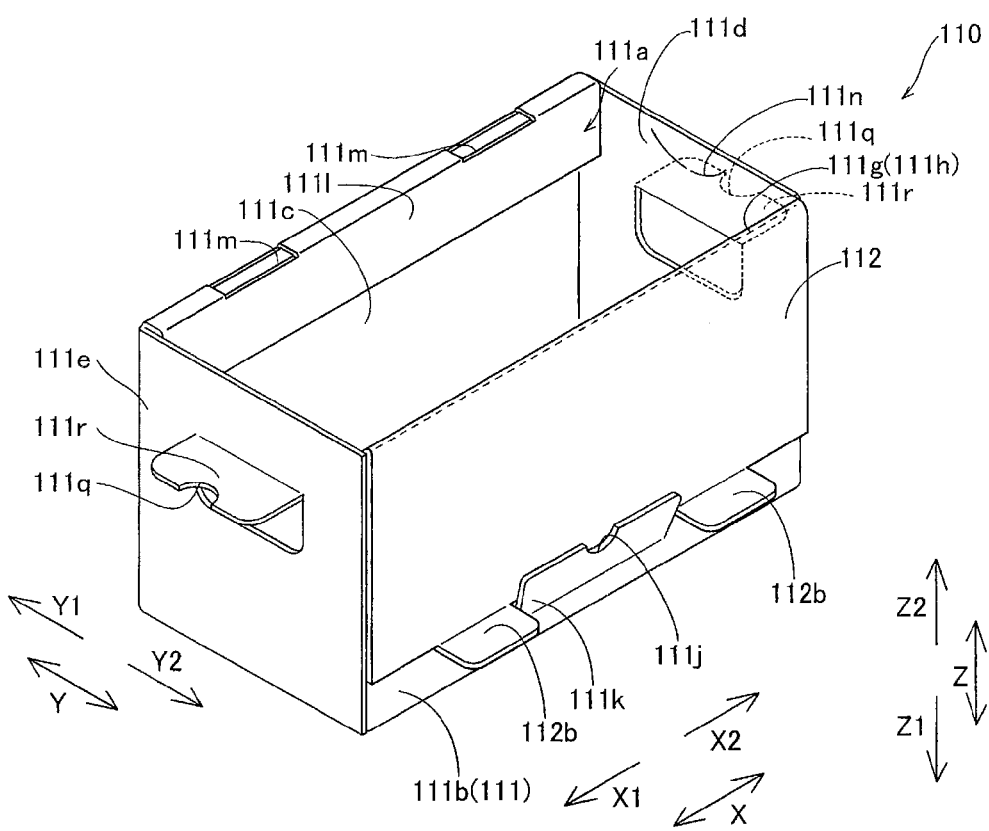
FIG. 11 is a perspective view showing the cover locked to the box in the first embodiment of the present invention.

In addition, as shown in FIG. 9, the cover 112 and the connector 111g are provided with a latched part 112a on the opposite side surface, and a pair of plugs 112b formed on both sides in the X direction of the latching part 112a. The length L1 in the X direction of the latched part 112a is greater than the length L2 in the X direction of the bottom end of the latch forming part 111i (latch 111k) on the one hand, and is less than the length L3 in the X direction of the top end of the latch forming part 111i (latch 111k). Thus, when the entire surface is in contact with the side surface 111b excluding the pair of plugs 112b of the cover 112, the latched part 112a (refer to FIG. 9) is latched by the latch 111k as shown in FIG. 11. The opening 111a of the box body 111 can therefore be maintained in an open state.

Note that when the latched part 112a is latched by the latch 111k, the latch 111k more securely latches the latched part 112a by having contact between the side surface on the latched part 112a side of the pair of plugs 112b and the side surface of both sides of the latch 111k in the X direction.

As shown in FIG. 9, a folding part 111l is formed by a fold at the top end (side in the arrow Z2 direction) of the side surface 111c on the side in the arrow Y1 direction. Since a flat surface is formed by the folding part 111l that has a width greater than the thickness (approximately 5 mm) at the top end of the side surface 111c, a user can avoid cutting a finger on the top end of the side surface 111c. The folding part 111l also has a pair of holes 111m into which fit the pair of plugs 112b of the cover 112 when the cover 112 is closed on the folding part 111l.

Figure 12:
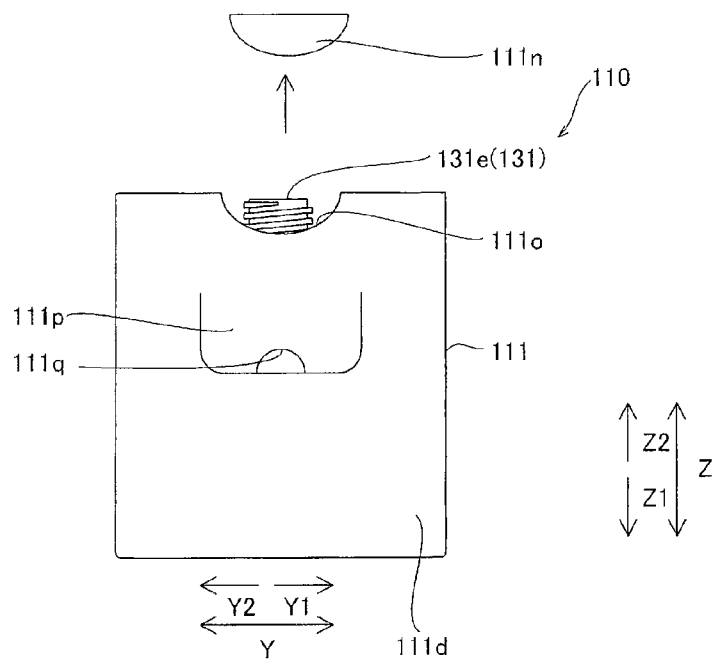
FIG. 12 is a side view showing the notched side after notching of the box of the first embodiment of the present invention.

As shown in FIG. 9, a notch forming part 111n is formed near the top end of the side surface 111d on the side in the arrow X2 direction, that is, in the approximate center in the Y direction. The notch forming part 111n is formed by pre-cutting through the side surface 111d, and is configured so that the notch forming part 111n can be detached along the pre-cut. In this case, a semi-elliptical notch 111o is formed by detaching the notch forming part 111n, as shown in FIG. 12.

The bottom end of the arc-shaped notch 111o is disposed on the side of the box body 111 in the arrow X2 direction, and is positioned at a location (position on the side in the arrow Z1 direction) lower than the top end of the opening 131e (described later) of the waste fluid container 131. Thus, the waste fluid of the waste fluid container 131 can be discharged to the outside through the notch 111o.

As shown in FIG. 9, a handle forming part 111p is also formed in the approximate center of the side surface 111d and side surface 111e. As shown in FIG. 11, a user can detach the handle forming part 111p (refer to FIG. 9) to form a handle 111r through the hole 111q formed at the bottom end of the handle forming part 111p.

Figure 13:
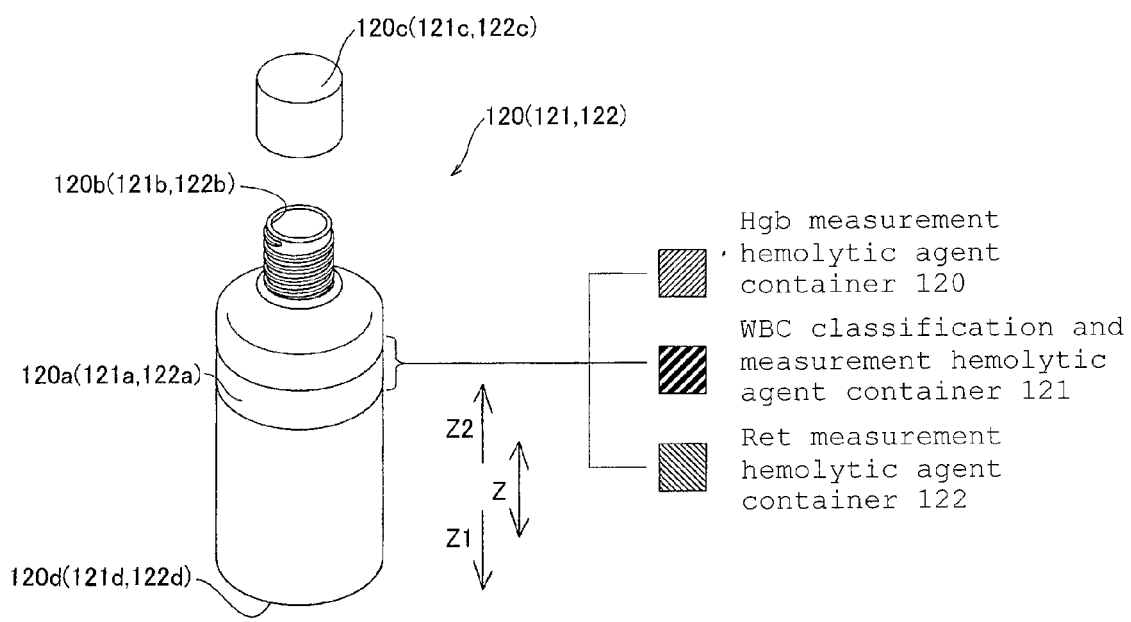
FIG. 13 is a perspective view showing the hemolytic agent container and staining agent container of the reagent set of the first embodiment of the present invention.

The hemolytic agent storage container 120, hemolytic agent storage container 121, and staining agent storage container 122 have the same shape and are configured by rigid plastic, as shown in FIG. 13. hemolytic agent storage container 120, hemolytic agent storage container 121, and staining agent storage container 122 are configured to be capable of accommodating approximately 250 mL of fluid.

As shown in FIG. 5, the hemolytic agent storage container 120, hemolytic agent storage container 121, and staining agent storage container 122 are arranged sequentially from the side in the arrow Y1 direction toward the side in the arrow Y2 direction. A blue identification marker 120a is provided on the side surface of the hemolytic agent storage container 120. A green identification marker 121a is provided on the side surface of the hemolytic agent storage container 121, and a red identification marker 122a is also provided on the side surface of the staining agent storage container 122.

As shown in FIG. 13, openings 120b, 121b, 122b for extracting the reagent container within are provided at the top of the hemolytic agent storage container 120, hemolytic storage container 121, and staining agent storage container 122. The openings 120b, 121b, 122b are configured to accept the insertion of the reagent aspirating tubes 103f, 103g, 103h, respectively, of the reagent extraction member 103 shown in FIG. 7. Thus, as shown in FIG. 1, the reagent in the hemolytic agent storage container 120, hemolytic agent storage container 121, and staining agent storage container 122 can be extracted by the sample analyzer 2 through the tubes 4a, 4b, and 4c of the reagent extraction units 103a, 103b, 103c of the reagent extracting member 103. The openings 120b, 121b, 122b are respectively sealed by screw-on caps 120c, 121c, 122c, which are manually screwed on the openings 120b, 121b, 122b, as shown in FIG. 13 before and after use of the reagent set 100.

Prior to use of the reagent set 100, a reagent (hemolytic agent) for hemoglobin measurement is accommodated in the hemolytic agent storage container 120, reagent (hemolytic agent) for white blood cell classification and measurement is accommodated in the hemolytic agent storage container 121, and reagent (staining agent) for reticulocyte measurement is accommodated in the staining agent storage container 122.

Figure 14:
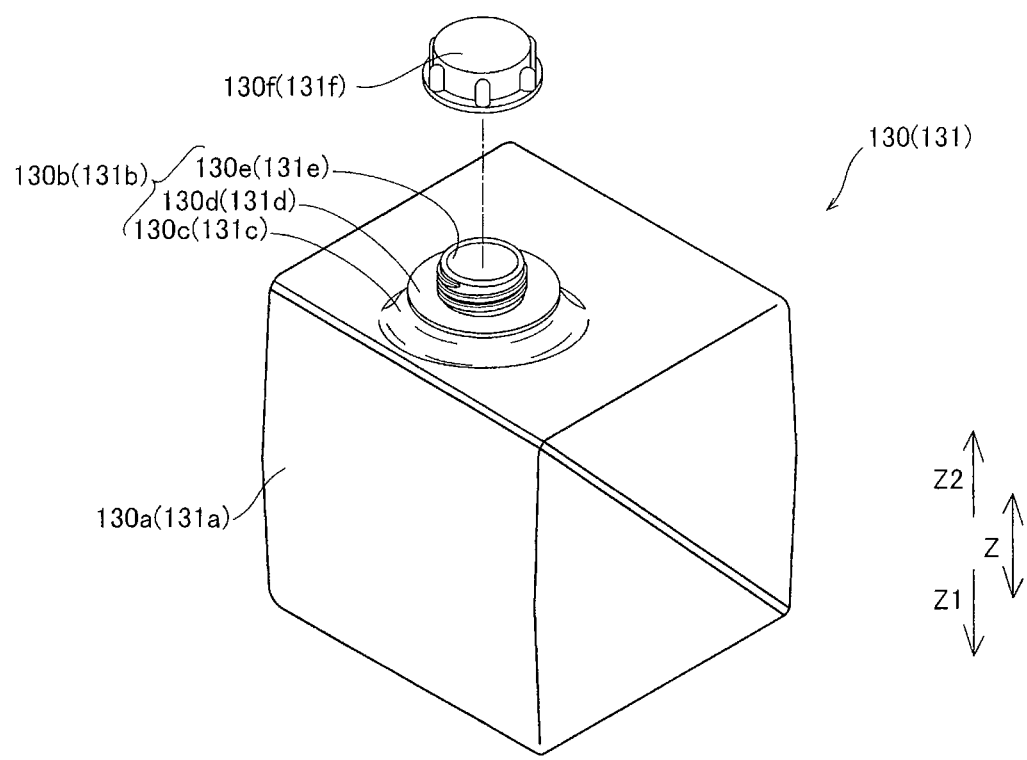
FIG. 14 is a perspective view showing the diluting liquid container and waste fluid container of the reagent set of the first embodiment of the present invention.

The diluting liquid container 130 and waste fluid container 131 are identical containers having a substantial cubic shape, as shown in FIG. 14. The diluting liquid container 130 also has a body 130a for accommodating the diluting liquid, and a protrusion 130b formed on the top surface (surface on the side in the arrow Z2 direction) of the body 130a. The waste fluid container 131 has a body 131a for collecting waste fluid, and a protrusion 131b formed on the top surface of the body 131a. The body 130a of the diluting liquid container 130 and the body 131a of the waste fluid container 131 are capable of accommodating approximately 5 liters of liquid, and have a property of flexibility so as to be capable of varying their shape. As shown in FIG. 6, the bottoms (side in the arrow Z1 direction) of the bodies 130a and 131a are supported by the bottom surface 111f of the box body 111l. That is, the diluting liquid container 130 and the waste fluid container 131 are disposed at substantially the same height within the box body 111.

As shown in FIG. 14, the protrusion 130b of the diluting liquid container 130 has a boundary part 130c positioned at the boundary with the top surface of the body 130a, a retainer 130d formed on the top of the boundary part 130c, and an opening 130e formed above the latch 130d. Similarly, the protrusion 131b of the waste fluid container 131 has a boundary part 131c positioned at the boundary with the top surface of the body 131a, retainer 131d formed on the top of the boundary part 131c, and an opening 131e formed above the latch 131d.

The boundary parts 130c and 131c have a bent shape, and are configured to be capable of projecting upward when stretched upward (side in the arrow Z2 direction) by a user. The retainers 130d and 131d are configured to lock on the top surface 113a (refer to FIG. 15) on the margin of the support holes 113e and 113f (to be described later). Note that the retainers 130d and 131d are substantially circular with a diameter of approximately 58 mm.

The openings 130e and 131e formed in the center of the protrusions 130b and 131b. Before and after use of the reagent set 100, the openings 130e and 131e are sealed by screwing on the caps 130f and 131f, respectively. Diluting liquid is accommodated in the diluting liquid container 130 prior to use of the reagent set 100.

Figure 6:
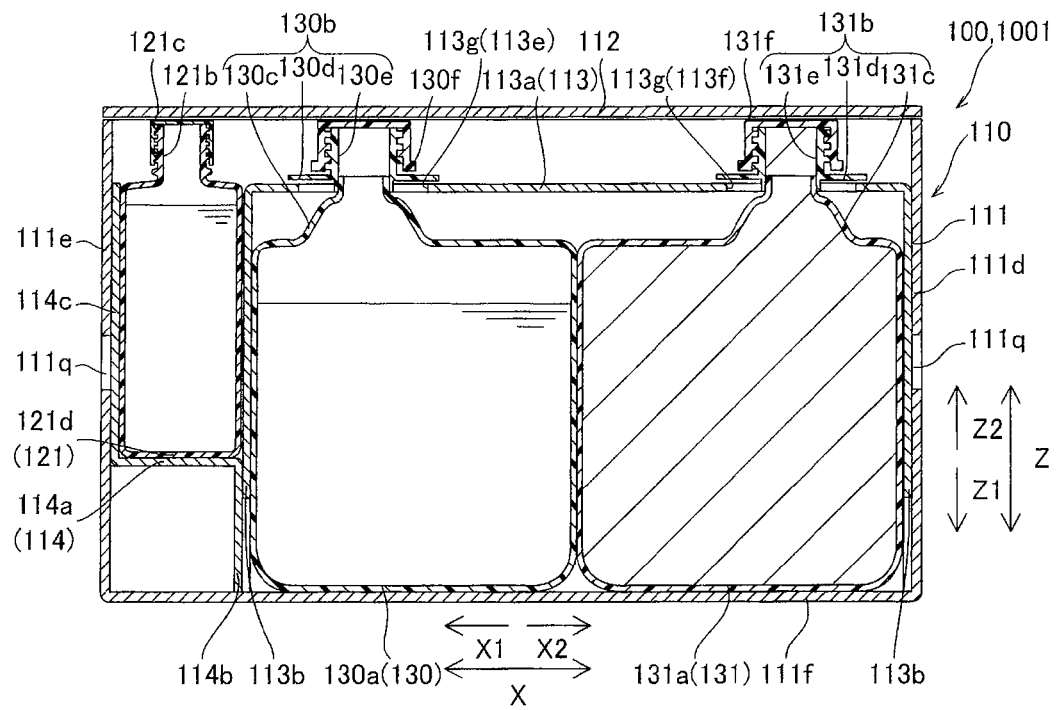
FIG. 6 is a cross sectional view along the 1000-1000 line of FIG. 2.

In the first embodiment, the opening 131e is sealed with gas (indicated by diagonal lines) entrapped in the body 131a of the waste fluid container 131 prior to use of the reagent set 100, as shown in FIG. 6. The waste fluid container 131 is configured to maintain a substantially cubic shape via the sealed in gas. Note that the gas is not entrapped to the point of completely expanding the body 131a of the waste fluid container 131 in order to prevent rupturing the body 131a of the waste fluid container 131. Note also that although the entrapped gas is gas in the first embodiment, other gases such as nitrogen gas may also be used.

As shown in FIG. 8, the waste fluid discharging tube 103*j* and the reagent aspirating tube 103*i* of the reagent extracting member 103 are respectively inserted into the openings 130*e* and 131*e*. The opening 130*e* of the diluting liquid container 130 is also configured so that the diluting liquid accommodated in the body 130*a* can be extracted by the sample analyzer 2 (refer to FIG. 1) through the reagent extractor 103*d* and tube 4*d* (refer to FIG. 1). The opening 131*e* of the waste fluid container 131 is configured to receive the inflowing waste fluid from the sample analyzer 2 through the waste fluid discharge unit 103*e* and tube 4*e* (refer to FIG. 1), and also is used as the discharge opening to discharge the waste fluid to the outside when waste fluid is accommodated in the body 131*a*.

As shown in FIG. 3, the opening 131*e* of the waste fluid container 131 is disposed near the side surface 111*d* on the side in the arrow X2 direction of the box body 111, and is positioned opposite the notch forming part 111*n* in the X direction.

Figure 15:
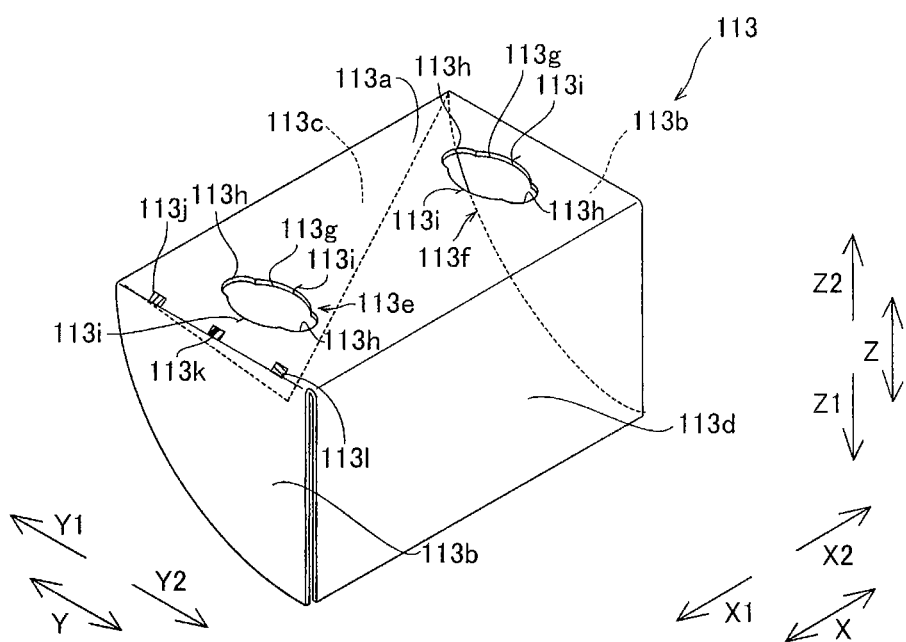
FIG. 15 is a perspective view showing the container holding member of the first embodiment of the reagent set of the present invention.

In the first embodiment, the container holding member 113 is configured of corrugated cardboard having a thickness of approximately 3 mm, and measures (external dimensions) approximately 338 mm in the X direction, 190 mm in the Y direction, and 190 mm in the Z direction, as shown in FIG. 15. As described above, the box body 111 (refer to FIG. 9) is configured of corrugated cardboard having a thickness of approximately 5 mm, and measures (external dimensions) approximately 205 mm in the Y direction. Thus, the gap in the Y direction between the container holding member 113 and the box body 111 is determined to be approximately 5 mm by subtracting the external dimension (approximately 190 mm) in the Y direction of the container holding member 113 and the thickness (approximately 2×5 mm) on the side in the arrow Y1 direction and side in the arrow Y1 direction of the box body 111 from the external dimension (approximately 205 mm) in the Y direction of the box body 111. Thus, the container holding member 113 can be held and anchored at a predetermined position within the box body 111 in the Y direction since there is a sufficiently small gap in the Y direction between the box body 111 and the container holding member 113.

The container holding member 113 includes a top surface 113*a*, a pair of side surfaces 113*b* extending downward (side in the arrow Z1 direction) from both edges in the X direction of the top surface 113*a*, a side surface 113*c* extending downward from the edge in the arrow Y1 direction of the top surface 113*a*, and side surface 113*d* extending downward from the edge on the side in the arrow Y2 direction of the top surface 113*a*.

Figure 16:
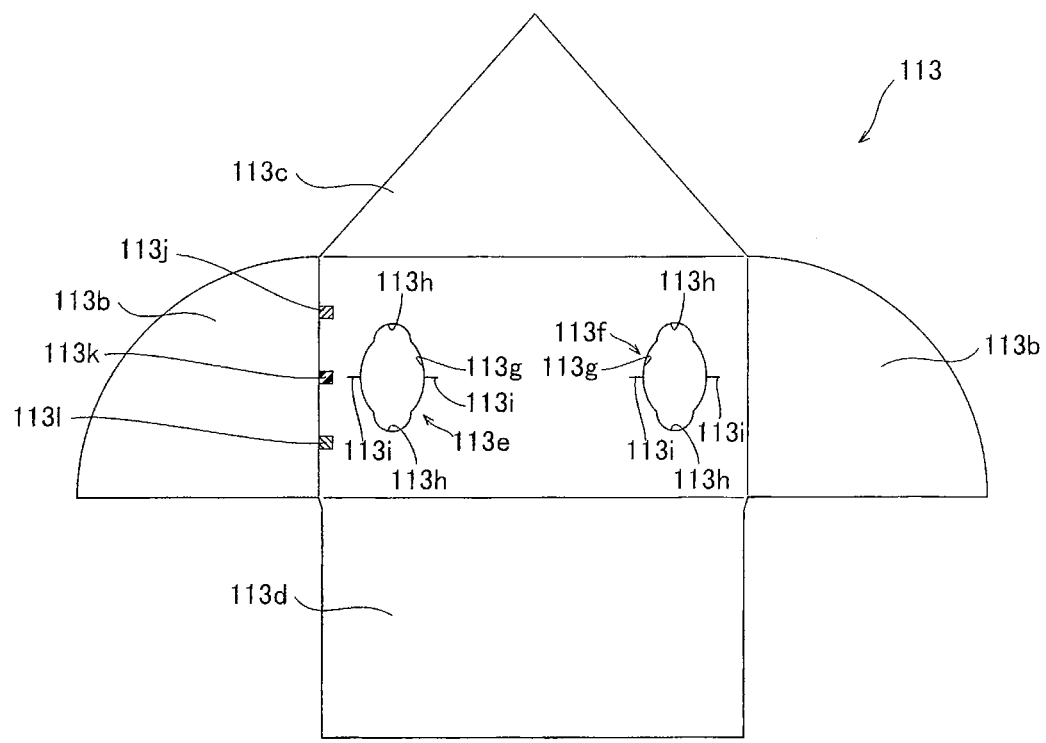
FIG. 16 is a development view showing the container holding member of the first embodiment of the reagent set of the present invention.
Figure 17:
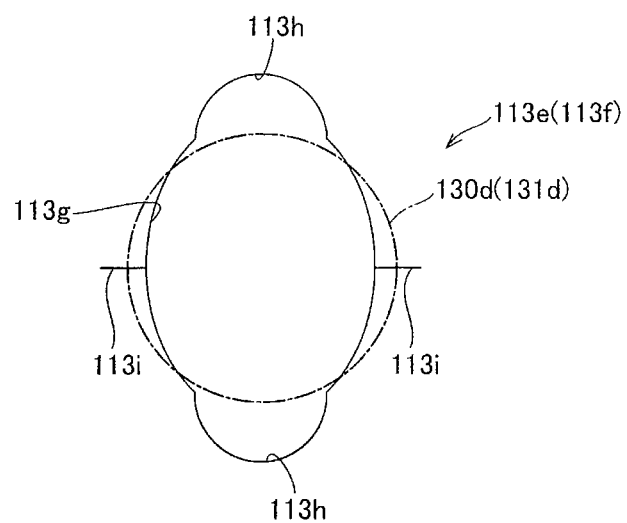
FIG. 17 is an enlarged plan view showing the holding hole of the container holding member of the first embodiment of the present invention.

As shown in FIGS. 15 and 16, a retaining hole 113*e* is formed near the edge in the arrow X1 direction of the top surface 113*a* to hold the protrusion 130*b* (refer to FIG. 14) of the diluting liquid container 130, and a retaining hole 113*f* is formed near the edge in the arrow X2 direction of the top surface 113*a* to hold the protrusion 131*b* (refer to FIG. 14) of the waste fluid container 131. As shown in FIG. 17, the retaining holes 113*e* and 113*f* are configured by an ovoid center hole 113*g*, pair of semicircular finger holes 113*h* formed at both ends in the Y direction of the center hole 113*g*, and pair of notches 113*i* formed at both ends in the X direction of the center hole 113*g*.

In the first embodiment, the length center hole 113*g* on the short side extending through the center in the X direction is approximately 50 mm. Thus, the retainers 130*d* and 131*d* lock to the top surface 113*a* at the margin of the retaining holes 113*e* and 113*f* since the length of the short side of the center hole 113*g* is shorter than the diameter (approximately 58 mm) of the substantially circular retainers 130*d* and 131*d*. The container holding member 113 therefore holds the diluting liquid container 130 and the waste fluid container 131 so that the openings 130*e* and 131*e* are respectively disposed at a predetermined position.

The pair of finger holes 113*h* are formed for the user to insert into the retaining holes 113*e* and 113*f* when removing the protrusions 130*b* and 131*b* from the below (the side in the arrow Z1 direction). The user easily removes the protrusions 130*b* and 131*b* by shifting the notch 113*i* in the Z direction.

As shown in FIG. 15, a blue identification marker 113*j*, green identification marker 113*k*, and red identification marker 113*l* are provided on the edge on the side in the arrow X1 direction of the top surface corresponding to the positions of the hemolytic agent storage container 120, hemolytic agent storage container 121, and staining agent storage container 122 (refer to FIG. 5). As shown in FIG. 5, the blue identification marker 113*j* on the side in the arrow Y1 direction is formed on the side in the arrow Y1 direction on the top surface 113*a*, and corresponds to the blue identification marker 120*a* on the side surface of the hemolytic agent storage container 120 on the side in the arrow Y1 direction. The center green identification marker 113*k* on the side in the arrow Y direction is formed at the center in the arrow Y direction on the top surface 113*a*, and corresponds to the green identification marker 121*a* on the side surface of the center hemolytic agent storage container 121 on the side in the arrow Y direction. The red identification marker 113*l* on the side in the arrow Y2 direction is formed on the side in the arrow Y2 direction on the top surface 113*a*, and corresponds to the red identification marker 122*a* on the side surface of the staining agent storage container 122 on the side in the arrow Y2 direction. That is, the blue identification markers 113*j* and 120*a* are markers identifying the container to the user as the hemolytic agent storage container 120; the green identification markers 113*k* and 121*a* are markers identifying the container to the user as the hemolytic agent storage container 121; and the red identification markers 113*l* and 122*a* are markers identifying the container to the user as the staining agent storage container 122.

In the first embodiment, as shown in FIG. 15, the corner on the side in the arrow Y1 direction, that is, below (side in the arrow Z1 direction) the pair of side surfaces 113*b*, is formed in a curved shape by beveling. This curve forms a circular arc-like part as the center of the corner on the side in the arrow Y2 direction, that is, the side in the arrow Z2 direction of the pair of side surfaces 113*b*. As shown in FIG. 5, when inserted into the box body 111, the side surface 113*b* in the arrow X2 direction is arranged so as to cover, from the inside of the box body 111, the hole 111*q* and handle 111*r* (refer to FIG. 11) formed by cutting away the handle forming part 111*p* of the side surface 111*d* of the box body 111. Thus, it is possible to prevent the shipper from coming into contact with the containers inside via the handle 111*r* and hole 111*q*.

The side surface 113*c* is formed as a rectangular equilateral triangle (refer to FIG. 16) with the apex positioned downward and the bottom edge positioned upward by beveling both corners in the X direction, that is, on the bottom (side in the arrow Z1 direction). The side surface 113*d* has a substantially rectangular shape, and covers, from the inside of the box body 111, the latch 111*k* (refer to FIG. 11) and hole 111*j* formed by cutting away the latch forming part 111*i* of the side surface 111*b* of the box body 111 when inserted into the box body 111, as shown in FIG. 5. Thus, it is possible to prevent the reagent and waste fluid of the reagent set 100 from adhering to the user via the latch 11k and hole 111j.

As shown in FIG. 6, the waste fluid container 131 is configured to abut the side surface 113b on the side in the arrow X1 direction of the container holding member 113, side surface 113c (refer to FIG. 15) on the side in the arrow Y1 direction of the container holding member 113, side surface 113d (refer to FIG. 15) on the side in the arrow Y2 direction of the container holding member 113 bottom surface 111f of the box body 111, and diluting agent container 130.

Figure 18:
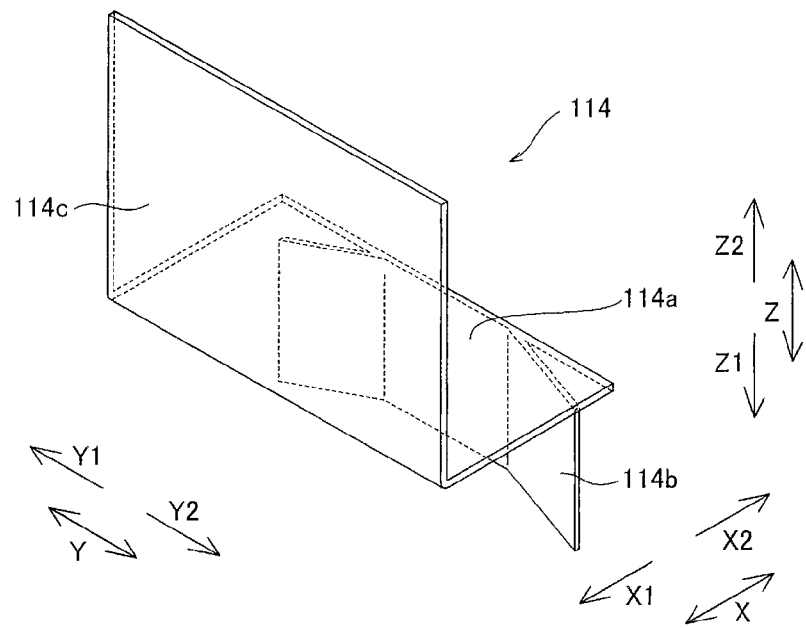
FIG. 18 is a perspective view showing the container holding member of the first embodiment of the reagent set of the present invention.

The container support member 114 is configured of corrugated cardboard having a thickness of approximately 3 mm, and measures (external dimensions) approximately 62 mm in the X direction, 190 mm in the Y direction, and 210 mm in the Z direction, as shown in FIG. 18. That is, the container support member 114 has a size of approximately 190 mm in the Y direction similar to the container holding member 113, such that the container support member 114 can be held and anchored within the box body 111.

The container support member 114 is configured by a supporting part 114a for supporting from below (side in the arrow Z2 direction) the bottom 120d of the hemolytic agent storage container 120, the bottom 121d of the hemolytic agent storage container 122 and the bottom 122d of the staining agent storage container 122, an arm 114b extending downward from the supporting part 114a side in the arrow X2 direction, an side surface 114c extending upward (side in the arrow Z1 direction) from the side of the supporting part 114a in the arrow X1 direction.

When the hemolytic agent storage container 120, hemolytic agent storage container 121, and staining agent storage container 122 are deployed on the supporting part 114a, the height of the arm 114b is set in the Z direction so that the height position of the openings 120b, 121b, 122b (refer to FIG. 13) is the same as the height position of the openings 130e of the diluting liquid container 130 and the opening 131e (refer to FIG. 14) of the waste fluid container 131 held on the container holding member 113. Thus, the bottom 120d of the hemolytic agent storage container 120, bottom 121d of the hemolytic agent storage container 121, and bottom 122d of the staining agent storage container 122 are disposed at higher positions than the bottoms (side in the arrow Z1 direction) of the main bodies 130a and 131a. Specifically, the height of the arm 114b in the Z direction is approximately 70 mm.

As shown in FIG. 5, when inserted into the box body 111, the side surface 114c is arranged so as to cover, from the inside of the box body 111, the hole 111q and handle 111r (refer to FIG. 11) formed by cutting away the handle forming part 111p of the side surface 111e of the box body 111. Thus, it is possible to prevent the reagent and waste fluid of the reagent set 100 from adhering to the user via the handle 111r and hole 111q.

The assembly sequence of the reagent set 100 of the first embodiment of the present invention is described below with reference to FIGS. 2, 3, 9, 14, and 19 through 22.

Figure 19:
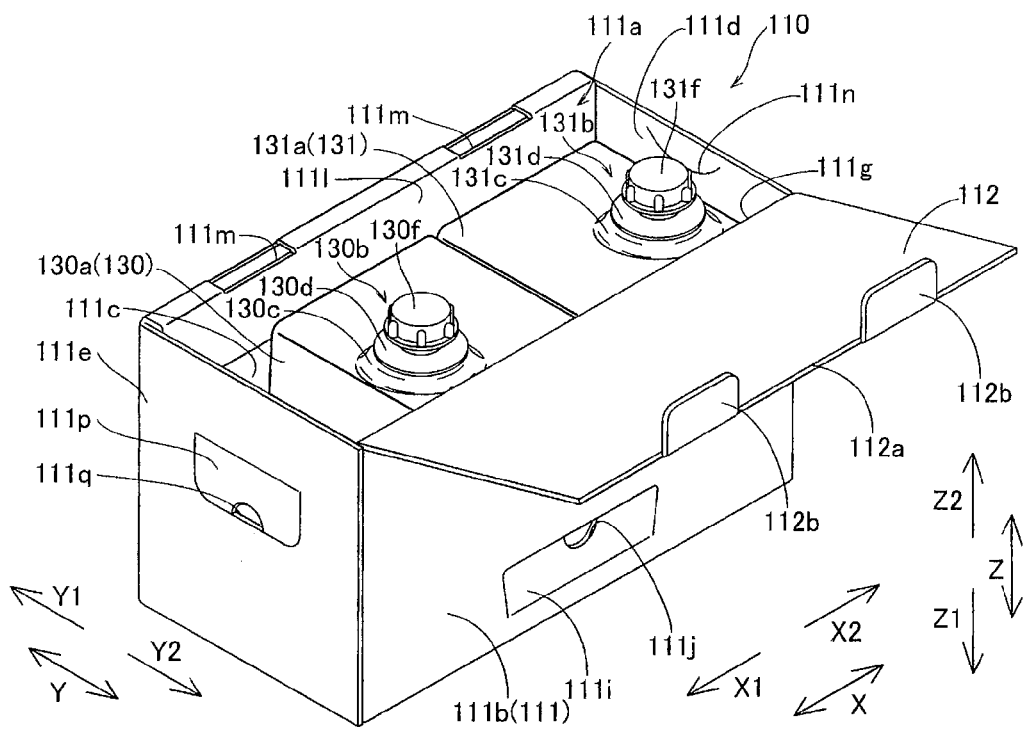
FIG. 19 is a perspective view illustrating the placement of the diluting liquid container and the waste container during the assembly of the reagent set of the first embodiment of the present invention.

First, the box 110 shown in FIG. 9 is prepared. As shown in FIG. 19, the diluting liquid container 130 accommodating the diluting liquid is disposed at the center in the X direction inside the box body 111, and the waste fluid container 131 with entrapped gas within is disposed at the side in the arrow X2 direction of the box body 111. Note that caps 130f and 131f are screwed on the opening 130e of the diluting liquid container 130 and the opening 131e of the waste fluid container 131, respectively.

Figure 20:
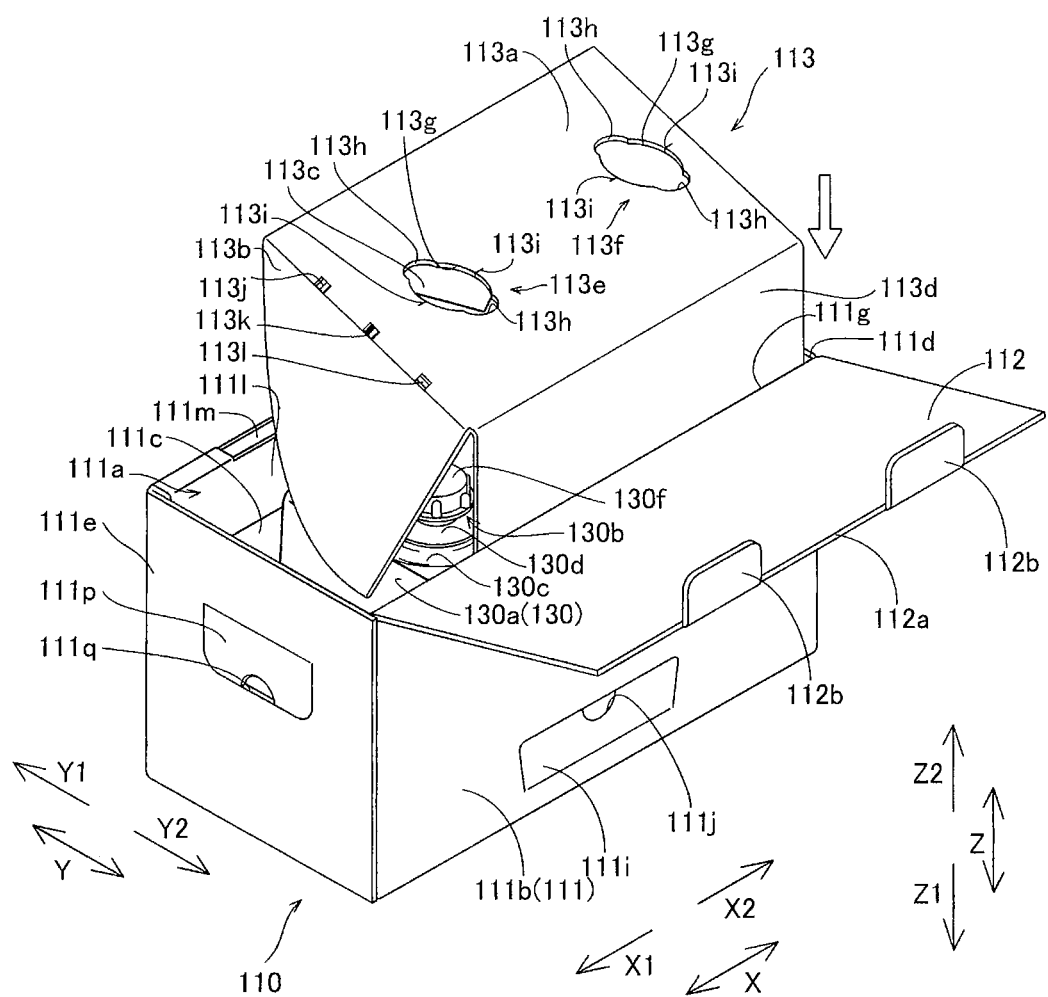
FIG. 20 is a perspective view illustrating the insertion of the container holding member during the assembly of the reagent set of the first embodiment of the present invention.

In the first embodiment, as shown in FIG. 20, the container holding member 113 is inserted so as to be held and anchored inside the box body 111 and cover the diluting liquid container 130 and waste fluid container 131 from (side in the arrow Z2 direction) above the box body 111. Specifically, the container holding member 113 is inserted so that the side surface 113d of the container holding member 113 on the side in the arrow Y2 direction is in a state of contact with the side surface 111b on the arrow Y2 direction side of the box body 111. Moreover, the container holding member 113 is inserted so that the side surface 113b on the arrow X1 direction side of the container holding member 113 contacts the side surface on the arrow X1 side of the diluting liquid container 130, and the side surface 113b on the arrow X2 direction side of the container holding member 113 is inserted between the side surface on the arrow X2 direction side of the waste fluid container 131 and the side surface 111d on the arrow X2 direction side of the box body 111. The side surface 113c on the arrow Y1 direction side of the container holding member 113 is also inserted between the side surface 111b on the arrow Y2 direction side of the box body 111 and the diluting liquid container 130 and waste fluid container 131.

In this case, the pair of side surfaces 113b are prevented from snagging downward (side in the arrow Z1 direction) on the side surface 111c on the arrow Y1 direction side of the box body 111 because the corner on the side in the arrow Y1 direction is beveled in a curved shape. The side surface 113c on the arrow Y1 side is also prevented from snagging downward (side in the arrow Z1 direction) by the body 111, diluting liquid container 130 and waste fluid container 131 because both corners in the X direction are beveled.

Figure 21:
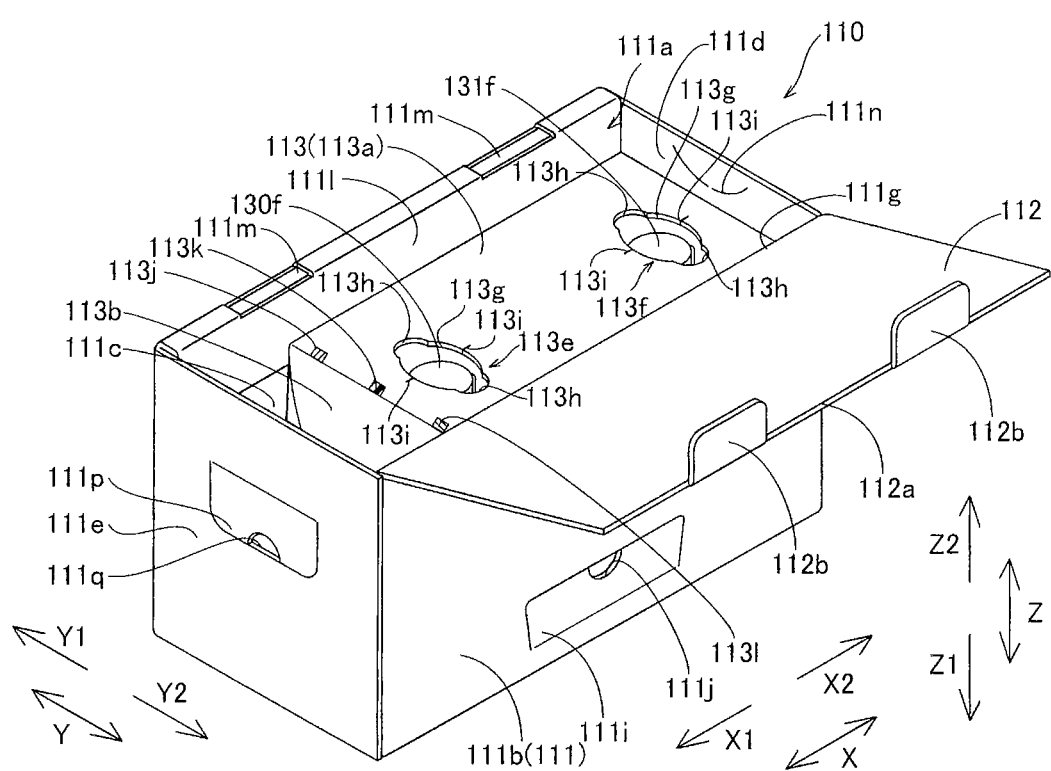
FIG. 21 is a perspective view illustrating the drawing of the protrusion of the diluting liquid container and the protrusion of the waste fluid container during the assembly of the reagent set of the first embodiment of the present invention.
Figure 22:
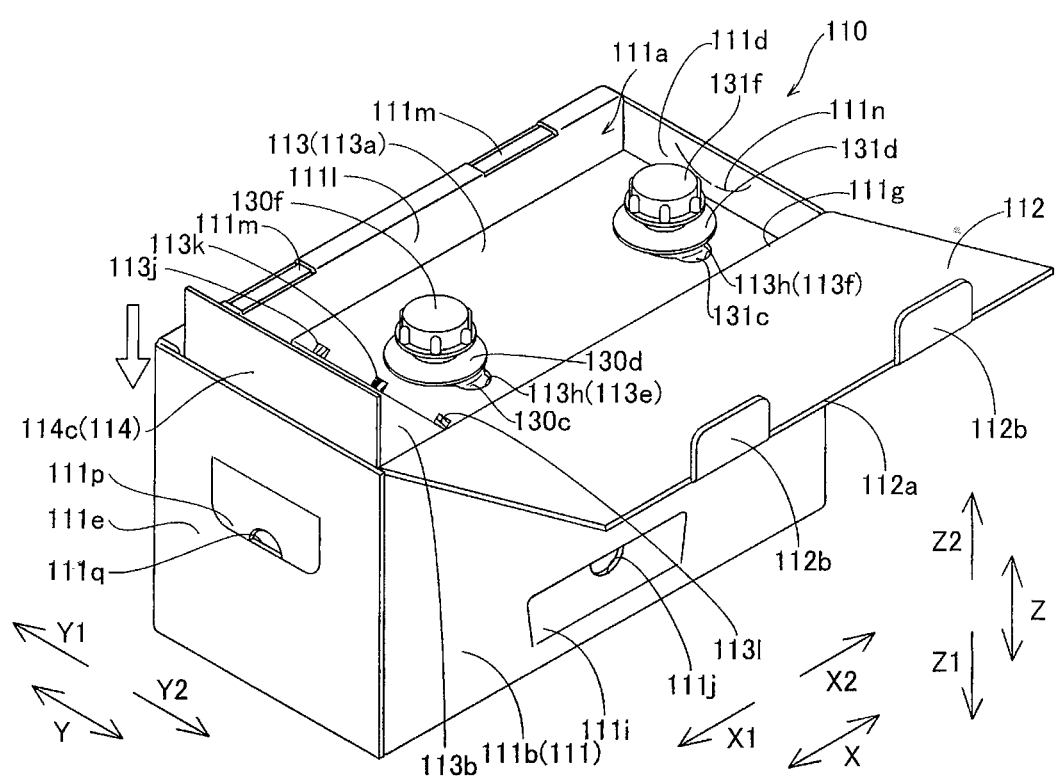
FIG. 22 is a perspective view illustrating the insertion of the container holding member during the assembly of the reagent set of the first embodiment of the present invention.

As shown in FIG. 21, thereafter, the protrusion 130b of the diluting liquid container 130 positioned below (side in the arrow Z1 direction) the top surface 113a of the container holding member 113 is withdrawn, and the protrusion 131b of the waste fluid container 131 is withdrawn. Specifically, the user inserts a finger in the pair of holes 113h of the retainer holes 113e and 113f to grab and withdraw the protrusions 130b and 131b. In this case, the protrusions 130b and 131b are withdrawn with the notches 113i of the retaining holes 113e and 113f dislocated in the Z direction. As shown in FIG. 22, the retainer 130d of the diluting liquid container 130 and the retainer 131d of the waste fluid container 131 are locked on the top surface 113a on the margin of the retaining holes 113e and 113f. Thereafter, the container support member 114 is inserted in the arrow X1 direction side inside the box body 111 with the side surface 114c of the container supporting member 114 in a state of contact with the side surface 111e on the arrow X1 direction side of the box body 111.

As shown in FIG. 3, the hemolytic agent storage container 120, hemolytic agent storage container 121, and staining agent storage container 122 are disposed on the arrow X1 direction side inside the box body 111. In this case, the hemolytic agent storage container 120, which corresponds to the identification marker 113j on the side in the arrow Y1 direction of the top surface 113a of the container holding member 113, is disposed on the side in the arrow Y1 direction. The hemolytic agent storage container 121, which corresponds to the identification marker 113k in the center of the top surface 113a, is disposed in the center in the Y direction. The staining agent storage container 122, which corresponds to the identification marker 113l on the side in the arrow Y2 direction of the top surface 113a, also is disposed on the side in the arrow Y2 direction. Note that caps 120c, 121c, and 122cf are screwed on the opening 121b of the hemolytic agent storage container 120, opening 121b of the hemolytic agent storage container 121, and opening 122b (refer to FIG. 13) of the staining agent storage container 122, respectively.

Finally, the opening 111a (refer to FIG. 3) of the box body 111 is closed with the cover 112 as shown in FIG. 2 by placing the pair of plugs 112b of the of the cover 112 in the holes 111m. The assembly of the reagent set 100 is thus complete.

The sequence for using the reagent set 100 of the first embodiment of the present invention is described below with reference to FIGS. 1 through 4, 8, 23, and 24.

Figure 23:
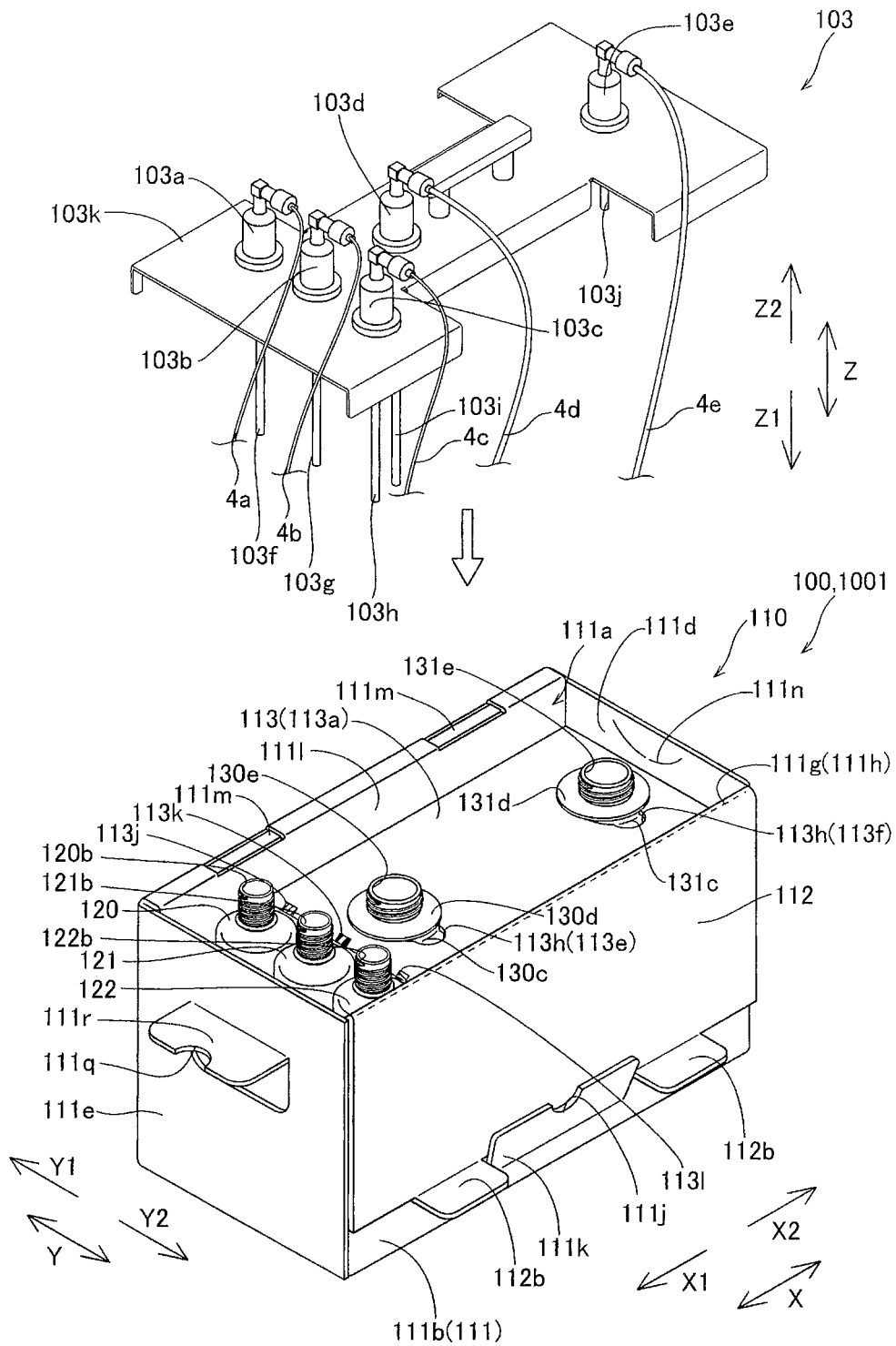
FIG. 23 is a perspective view illustrating the placement of the reagent removal member during use of the reagent set of the first embodiment of the present invention.

To carry the reagent set 100, the user forms the handle 111r by removing the handle forming part 111p (refer to FIG. 3) provided on the side surfaces 111d and 111e of the box body 111, as shown in FIG. 23. The user then carries the reagent set 100 (box body 111) while supporting both sides in the X direction.

When using the reagent set 100, the user opens the cover 112 mounted on the box body 111 from the state shown in FIG. 2, as shown in FIG. 3. The user then removes the latch forming part 111i to form a latch 111k (refer to FIG. 23). As shown in FIG. 23, the latched part 112a (refer to FIG. 3) of the cover 112 is locked to the latch 111k.

The caps 120c, 121c, 122c, 130f, 131f (refer to FIG. 3) are then unscrewed from the openings 120b, 121b, 122b, 130e and 131e. Thereafter, the user disposes the reagent extraction member 103 so as to cover the opening 111a from above (side in the arrow Z2 direction) the box body 111. In this case, the reagent aspirating tubes 103f, 103g, 103h, and 103i are inserted into the openings 120b, 121b, 122b, and 130e, respectively, and the waste fluid discharging tube 103j of the waste fluid discharging unit 103e is inserted into the opening 131e.

As shown in FIG. 1, the reagents accommodated in the hemolytic agent storage container 120, hemolytic agent storage container 121, and staining agent storage container 122 are fed to the sample analyzer 2 through the reagent extraction units 103a, 103b, 103c, and 103d, and tubes 4a, 4b, 4c, and 4d by the user operating the sample analyzer 2. After the reagent has been used in the analysis of the sample (not shown in the drawing) in the sample analyzer 2, the reagents are recovered by the waste fluid container 131 as waste fluid.

When all reagent accommodated in the hemolytic agent storage container 120, hemolytic agent storage container 121, staining agent storage container 122, or diluting liquid accommodated in the diluting liquid container 130 is completely used in the sample analyzer 2 by performing sample analyses a predetermined number of times in the sample analyzer 2, a message (not shown in the drawing) indicating the need to replace the reagent set 100 is displayed on the sample analyzer 2, and use of the reagent set 100 ends. The waste fluid from the used reagent accommodated in the hemolytic agent storage container 120, hemolytic agent storage container 121, staining agent storage container 122, and the diluting liquid accommodated in the diluting agent container 130 is collected in the body 131a of the waste fluid container 131.

Then, after the reagent extraction member 103 has been removed from the reagent set 100, a new reagent set 100 can be prepared and the reagent extraction member 103 can be mounted in the new reagent set 100 as shown in FIG. 1. As shown in FIG. 4, the user screws the caps 120c, 121c, 122c, 130f, and 131f on the respective openings 120b, 121b, 122b, 130e, and 131e (refer to FIG. 23).

Thereafter, the user closes the opening 111a of the box body 111 via the cover 112 as shown in FIG. 2. Then, the used reagent set 100 is stored in a predetermined location, and all reagent sets 100 are disposed of together, or the waste fluid collected in the waste fluid container 131 is disposed of separately by itself.

Figure 24:
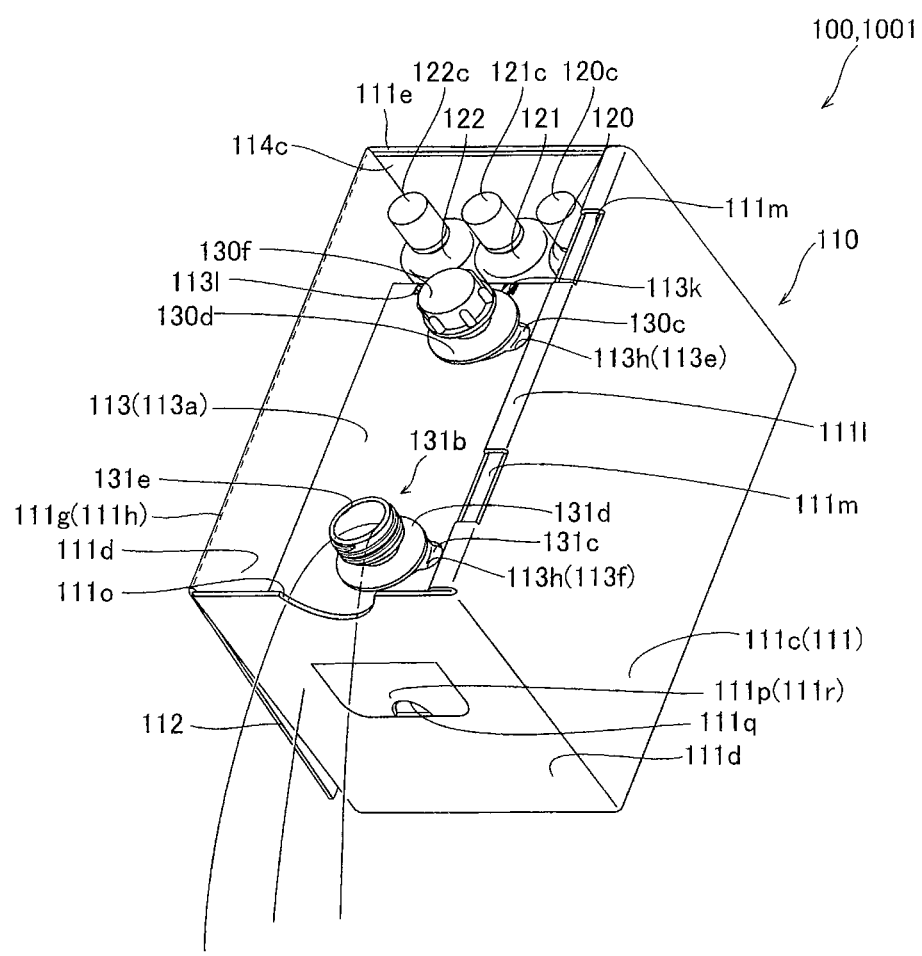
FIG. 24 is a perspective view illustrating the discharge of the waste fluid from the waste fluid container to the outside during use of the reagent set of the first embodiment of the present invention.

Note that when the waste fluid collected in the waste fluid container 131 is disposed of separately, the user first opens the cover 112 mounted on the box body 111 as shown in FIG. 3. As shown in FIG. 24, the notch forming part 111n (refer to FIG. 23) provided on the side surface 111d of the box body 111 is then removed to form a notch 111o, and the cap 131f (refer to FIG. 3) screwed on the opening 131e of the waste fluid container 131 is removed. Thereafter, the user inclines the reagent set 100 so that the side surface 111d on the side in the arrow X2 direction of the box body 111 is lower than the side surface 111e on the side in the arrow X1 direction. Thus, the waste fluid of the waste fluid container 131 is discharged toward the center direction of the side surface 111d of the box body 111 and outside the box. In this case, the waste fluid of the waste fluid container 131 is discharged from the opening 131e of the waste fluid container 131 through the notch 111o.

As described above in the first embodiment, the container holding member 113 prevents dislocation of the opening 130e of the diluting liquid container 130 and the opening 131e of the waste fluid container 131 from the predetermined positions even when the reagent set 100 is inclined during transport or the like by providing the container holding member 113 for holding the diluting liquid container 130 and the waste fluid container 131 so as to dispose the openings 130e and 131e at the predetermined positions. Thus, it is possible to prevent difficulty when inserting the reagent aspirating tube 103i and waste fluid discharging tube 103j into the openings 103e and 131e, respectively, so that handling is easier than conventionally. The diluting liquid container 130 must have a relatively large capacity when using large amounts of diluting fluid. Although in this case the weight of the diluting liquid container 130 is increased, which increases the likelihood that the diluting liquid container 130 will dislocate from the predetermined position when the reagent set 100 is inclined during transport or the like, such positional dislocation is prevented by the structure of the present invention.

As described above in the first embodiment, the lower corners of the side surface 113b are prevented from snagging on the side surface 111c on the side in the arrow Y1 direction of the box body 111 when the container holding member 113 is inserted, anchored, and supported inside the box body 111 by the curved shape of the corners formed by beveling the corners on the side in the arrow Y1 direction, that is the lower corners of the pair of side surfaces 113b of the container holding member 113. Thus, the container holding member 113 can be easily inserted into the box body 111. Moreover, the container holding member 113 can be inserted into the box more easily than when the corners are straight.

As described above in the first embodiment, it is possible to prevent the lower corners of the side surface 113c from snagging on the box body 111, waste fluid container 131 and diluting liquid container 130 when the container holding member 113 is inserted, anchored and supported inside the box body 111 by forming the side surface 113c of the container holding member 113 as a rectangular equilateral triangle with the apex positioned downward and the bottom edge position upward. Thus, the container holding member 113 can be easily inserted into the box body 111.

As described above in the first embodiment, impact shocks received by the diluting liquid container 130 during transport and the like can be cushioned by the cushioning effect of the waste fluid container 131 by filling the waste fluid container 131 with a gas (indicated by diagonal lines) and sealing the opening 131e with the cap 131f prior to using the reagent set 100. Thus, it is possible to prevent damage to the diluting liquid container 130 caused by such impact shocks.

As described above in the first embodiment, it is possible to prevent difficulty when inserting the reagent aspirating tubes 103f, 103g, 103h, 103i, and waste fluid discharging tube 103j into the respective openings 120b, 121b, 122b, 130e, and 131e compared to when there is a large difference in the height positions of the openings 120b, 121b, 122b, 130e, and 131e by providing the arm 114b to maintain the height position of the openings 120b, 121b, 122b and the height positions of the opening 130e of the diluting liquid container 130 and the opening 131e of the waste fluid container 131 are substantially identical height positions when the hemolytic agent storage container 120, hemolytic agent storage container 121, and staining agent storage container 122 are disposed on the support 114a of the container supporting member 114.

As described above in the first embodiment, impact shocks received by the diluting liquid container 130 during transport and the like can be cushioned by the container supporting member 114 and waste fluid container 131 by arranging the diluting liquid container 130 in the X direction between the container supporting member 114 disposed on the side in the arrow X1 direction and the waste fluid container 131 disposed on the side in the arrow X2 direction. Thus, it is possible to prevent damage to the diluting liquid container 130 caused by such impact shocks.

As described above in the first embodiment, hemolytic agent storage container 120 provided with the identification marker 120a that corresponds to the identification marker 113j, the hemolytic agent storage container 121 provided with the identification marker 121a that corresponds to the identification marker 113k, and the staining agent storage container 122 provided with the identification marker 122a that corresponds to the identification marker 113l may be disposed at the respective locations provided with the identification markers 113j, 113k, and 113l by forming the blue identification marker 113j, green identification marker 113k, and red identification marker 113l on the edge on the side in the arrow X1 direction of the top surface 113a in correspondence with the positions of deployment of the hemolytic agent storage container 120, hemolytic agent storage container 121, and staining agent storage container 122. Therefore, it is possible to prevent erroneous placement of the hemolytic agent storage container 120, hemolytic agent storage container 121, and staining agent storage container 122 at the wrong positions.

As described above in the first embodiment, impaired operation during use of the reagent set 100 caused by the opening 111a being blocked by the cover 112 can be prevented since blocking of the opening 111a by the cover 112 is prevented by the latch 111k and latched part 112a during use of the reagent set 100 by maintaining the opening 111a of the box body 111 in an open state by locking the latched part 112a of the cover 112 to the latch 111k of the box body 111.

As described above in the first embodiment, waste fluid discharged from the waste fluid container 131 is discharged so as to pass through the notch 111o when the user discharges the waste fluid by forming the notch 111o from the notch forming part 111n by forming the notch forming part 111n in the center part in the Y direction near the top end of the side surface 111d of the box body 111. Thus, the discharging waste fluid is prevented from adhering to the side surface 111d of the box body 111. Furthermore, the reagent and waste fluid of the reagent set 100 is prevented from adhering to the user through the notch 111o because the notch 111o is not present before the notch 111o is formed.

As described above in the first embodiment, the openings 130e and 131e are easily held at predetermined positions simply by holding the protrusions 130b and 131b via the holes 113e and 113f by forming the hold 113e for holding the protrusion 130b of the diluting liquid container 130 near the edge in the arrow X1 direction of the top surface 113a of the container holding member 113, and forming the hole 113f for holding the protrusion 131b of the waste fluid container 131 near the edge in the arrow X2 direction of the top surface 113a.

As described above in the first embodiment, the environmental burden (adverse effects) can be reduced compared to when plastic containers are used since the containers are easily reused by forming the box body 111, container holding member 113, and container supporting member 114 of corrugated cardboard.

As described above in the first embodiment, the diluting fluid and reagent supplied from the diluting liquid container 130 and used by the sample analyzer 2 can then be collected as waste fluid in the waste fluid container 131 without excessively increasing the size of the reagent set 100 by configuring the diluting liquid container 130 and waste fluid container 131 to have the same volume capacity.

As described above in the first embodiment, the reagent aspirating tube 103i and waste fluid discharging tube 103j are anchored in correspondence to the predetermined positions of the respective openings 130e and 131e in the present invention to prevent dislocation of the opening 130e of the diluting liquid container 130 and opening 131e of the waste fluid container 131 from their predetermined positions by anchoring and holding the reagent aspirating tube 103i and waste fluid discharging tube 103j so as to not vary their mutual positions via the metal plate 103k. Thus, the reagent aspirating tube 103i and waste fluid discharging tube 103j can be more easily inserted into the respective openings 130e and 131e.

(Second Embodiment)

A second embodiment is described below with reference to FIGS. 25 through 41. The second embodiment is described by way of example in which the notch is preformed, unlike the first embodiment.

The overall structure of the reagent set 200 of the second embodiment of the present invention is described below with reference to FIGS. 25 through 38.

Figure 25:
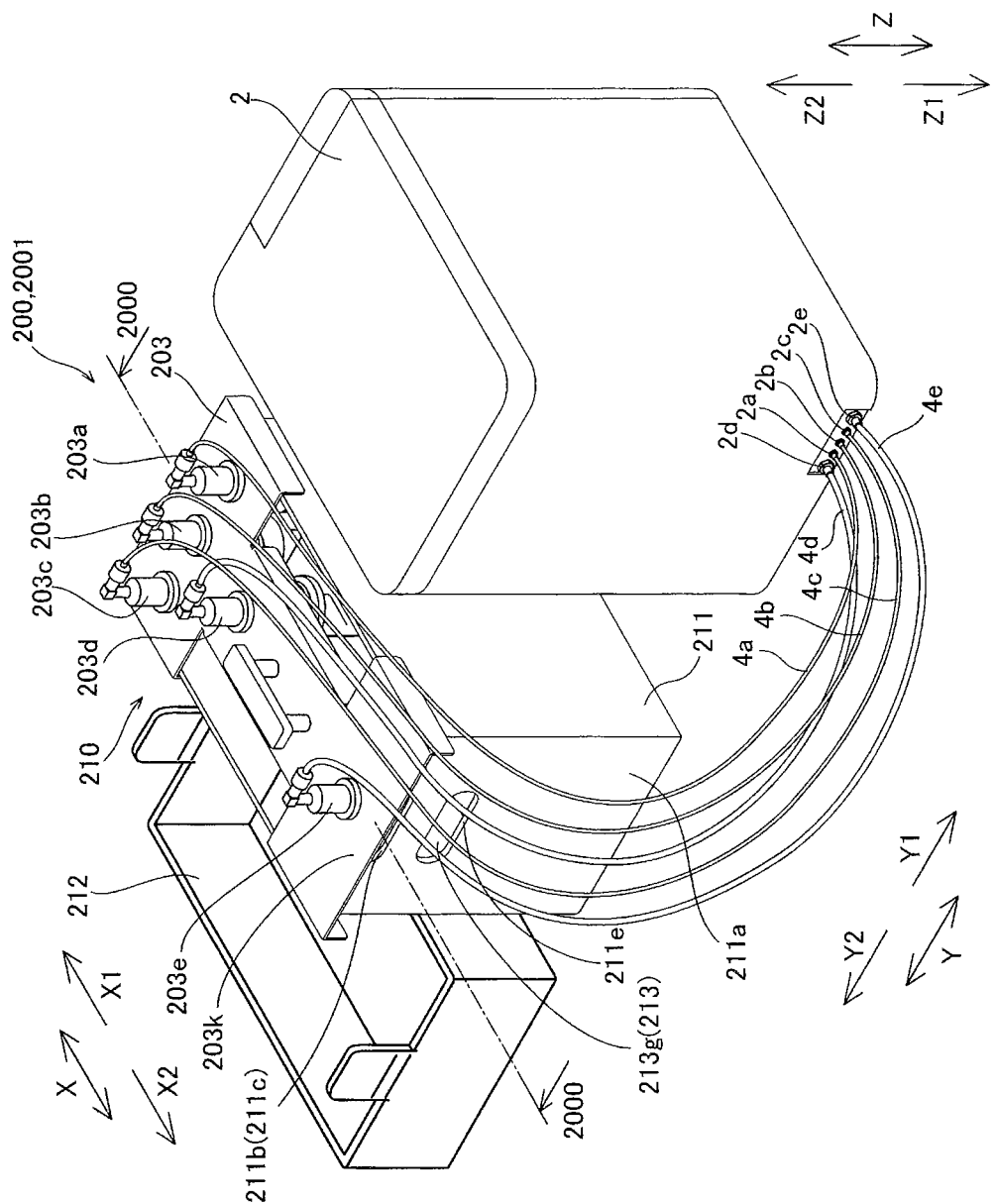
FIG. 25 is a perspective view showing the structure of the reagent removal member, sample analyzer, and reagent set of a second embodiment of the present invention.
Figure 26:
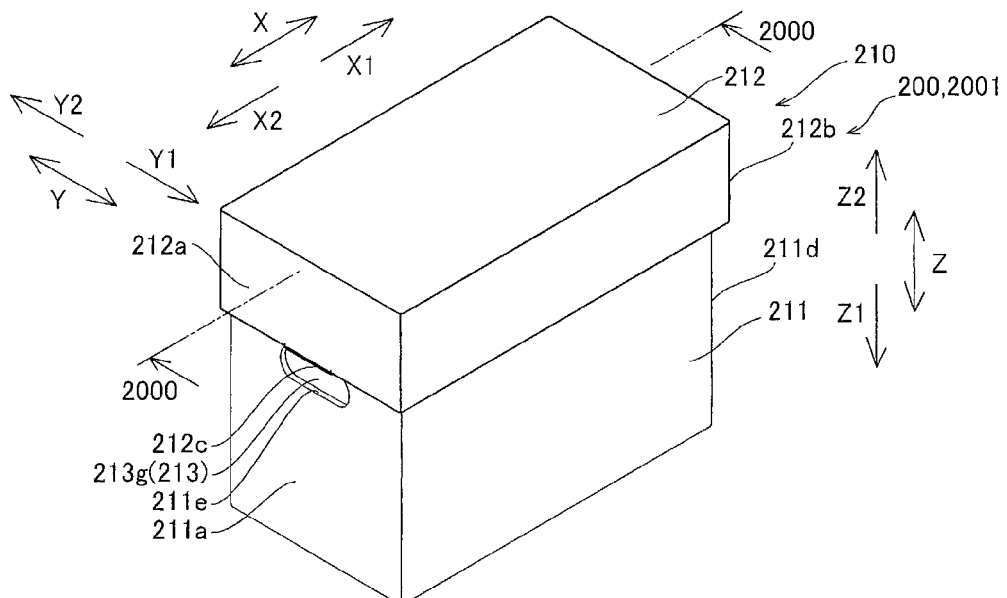
FIG. 26 is a perspective view showing the exterior of the reagent set of the second embodiment of the present invention.
Figure 28:
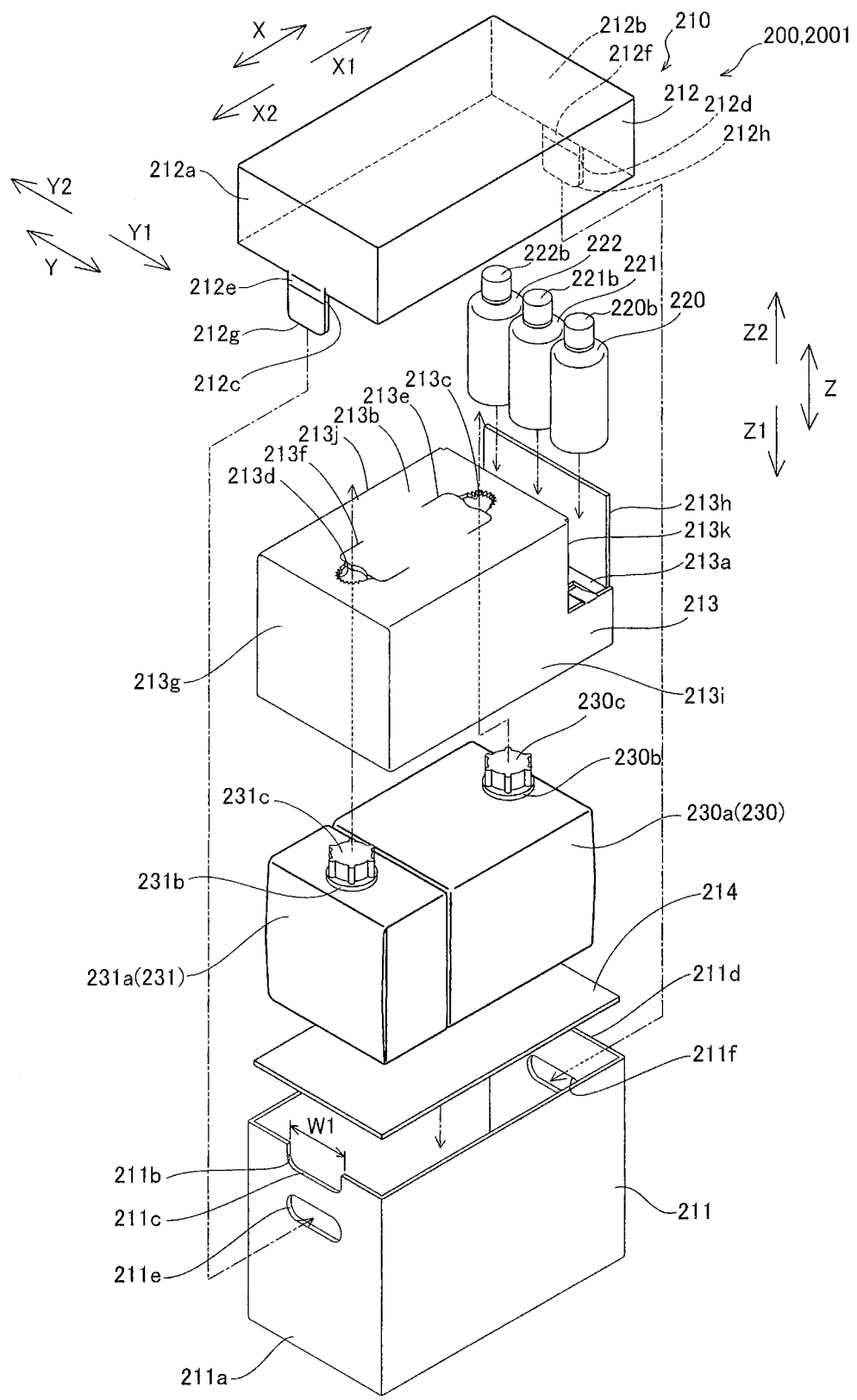
FIG. 28 is an exploded perspective view showing the general structure of the second embodiment of the reagent set of the present invention.

As shown in FIG. 25, the reagent set 200 of the second embodiment is connected to a sample analyzer 2 for analyzing blood via a reagent extraction member 203 while a cover 212 is removed from a container 210 (described later). The reagent set 200 includes a reagent container 2001, and reagent accommodated in each reagent storage container of the reagent container 2001. As shown in FIG. 28, the reagent container 2001 includes a box 200, interior member (container holding member) 213 disposed within the box 200, mat 214 disposed between the interior member 213 and the inner bottom surface of the box 200, hemolytic agent storage containers 220 and 221, staining agent storage container 222, diluting liquid container 230, and waste fluid container 231. The box 200 includes a box body 211 that is open on the top end side (side in the arrow Z2 direction and positioned at the bottom (side in the arrow Z1 direction) of the box 200, a cover 212 that is mountable on the box body 211 so as to close the top end of the box body 211 by covering the box body 211 from above (side in the arrow Z2 direction). The box body 211 measures approximately 360 mm in the X direction, approximately 200 mm in the Y direction, and approximately 200 mm in the Z direction, as shown in FIG. 26.

Inside the box body 211, the hemolytic agent storage containers 220 and 221 are disposed on the side on the arrow X1 direction of the box body 211, the staining agent storage container 222 is disposed on the side in the arrow X1 direction of the box body 211, the diluting liquid container 230 (refer to FIG. 28) is disposed in the center in the X direction of the box body 211, and the waste fluid container 231 (refer to FIG. 28) is disposed on the side in the arrow X2 direction of the box body 211.

In addition, as shown in FIG. 25, during use of the reagent set 200, the cover 212 is removed from the box body 211, and the reagent extraction member 203 is disposed so as to cover the box body 211 from above (side in the arrow Z2 direction). The reagent extraction member 203 is provided with reagent extraction units 203a, 203b, 203c, 203d, and 203e respectively corresponding to the hemolytic agent storage containers 220, 221, staining agent storage container 222, diluting liquid container 230, and waste fluid container 231. The reagent extraction units 203a, 203b, and 203c include reagent aspirating tubes 203g for aspirating reagent, and the reagent extraction unit 203d includes a reagent aspirating tube 203i for aspirating diluting liquid. The waste discharging unit 203e also includes a waste fluid discharging tube 203j for discharging waste fluid. The reagent extraction units 203a, 203b, 203c, 203d and the waste fluid discharging unit 203e are anchored to a metal plate 203k.

Figure 27:
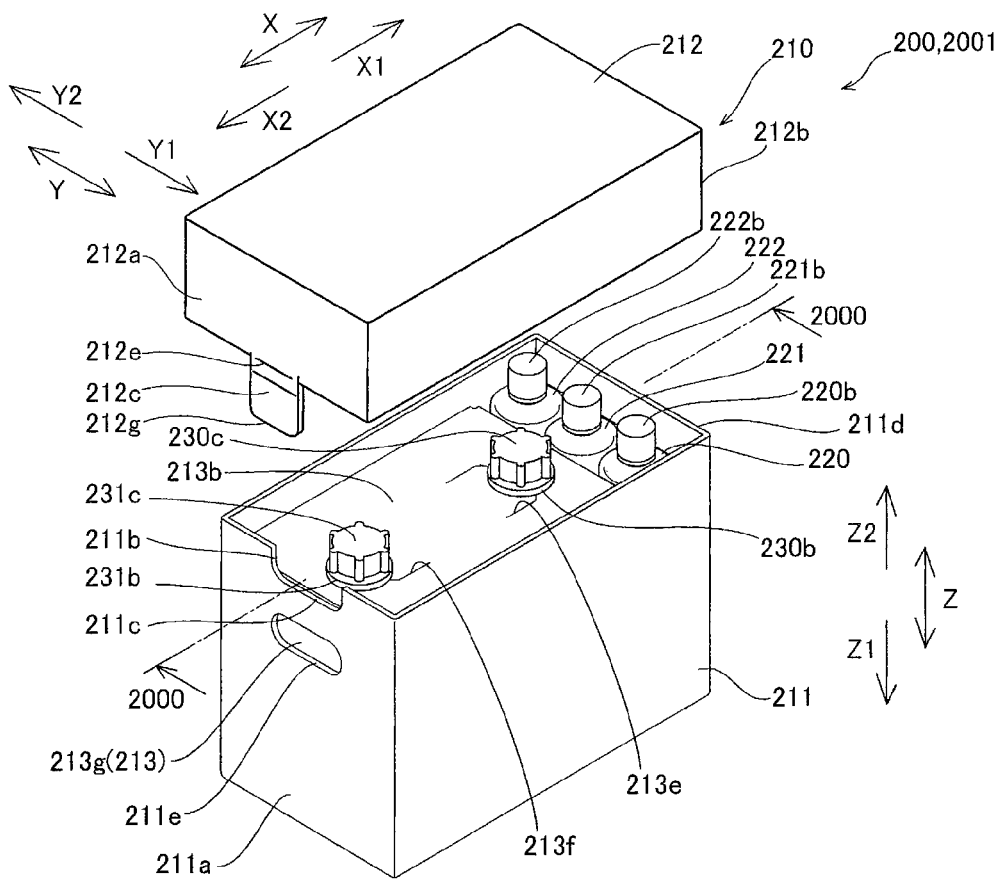
FIG. 27 is a perspective view showing the structure of the reagent set of the second embodiment of the present invention.
Figure 31:
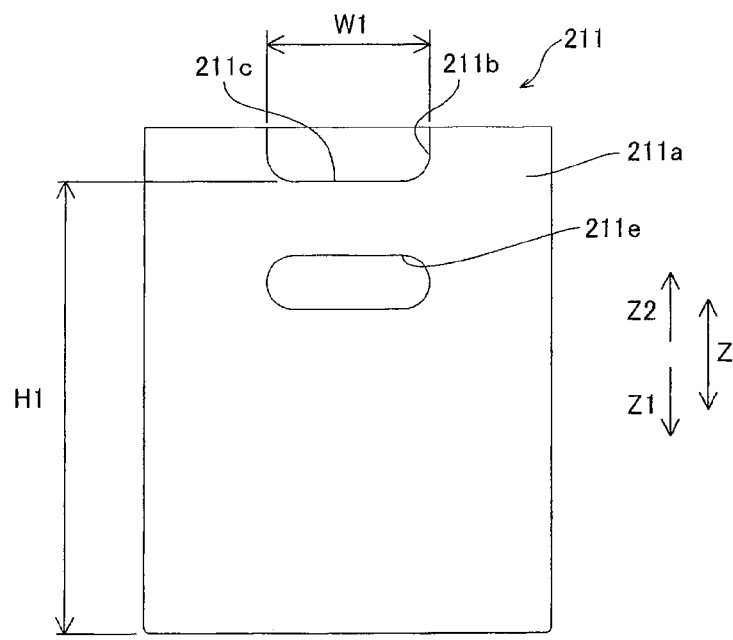
FIG. 31 is a side view showing the notched side of the box body of the reagent set of the second embodiment of the present invention.
Figure 32:
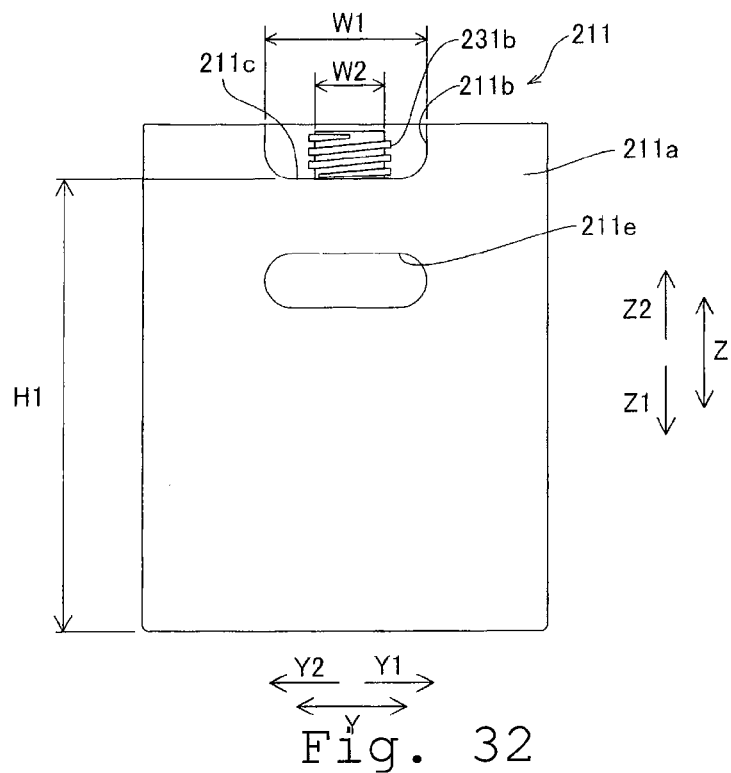
FIG. 32 is a side view showing the positional relationship of the notch of the box body and the discharge opening of the waste fluid container of the reagent set of the second embodiment of the present invention.

In the second embodiment, as shown in FIGS. 27 and 28, the side surfaces 211a of the box body 211 are provided on the side in the arrow X1 direction, side in the arrow X2 direction, side in the arrow Y1 direction, and side in the arrow Y2 direction, respectively. Among the side surfaces 211a of the box body 211, a notch 211b is provided at the top end of the side surface 211a on the side in the arrow X2 direction nearest the opening 231b (described later) of the waste fluid container 231. As shown in FIG. 31, the notch 211b is formed in the center in the arrow Y direction on the top end of the side surface 211a, and has a width W1 of approximately half the top end of the side surface 211a. As shown in FIG. 32, the width W1 of the notch 211b is greater than the width W2 of the opening 231b of the waste fluid container 231, and the notch 211b is provided to overlap the entirety of the width W2 of the opening 231b of the waste fluid container 231. The notch 211b has a substantially rectangular shape with the length of the side in the Y direction greater than the length of the side in the Z direction. The bottom 211c of the notch 211b has a height H1 in the Z direction.

Figure 29:
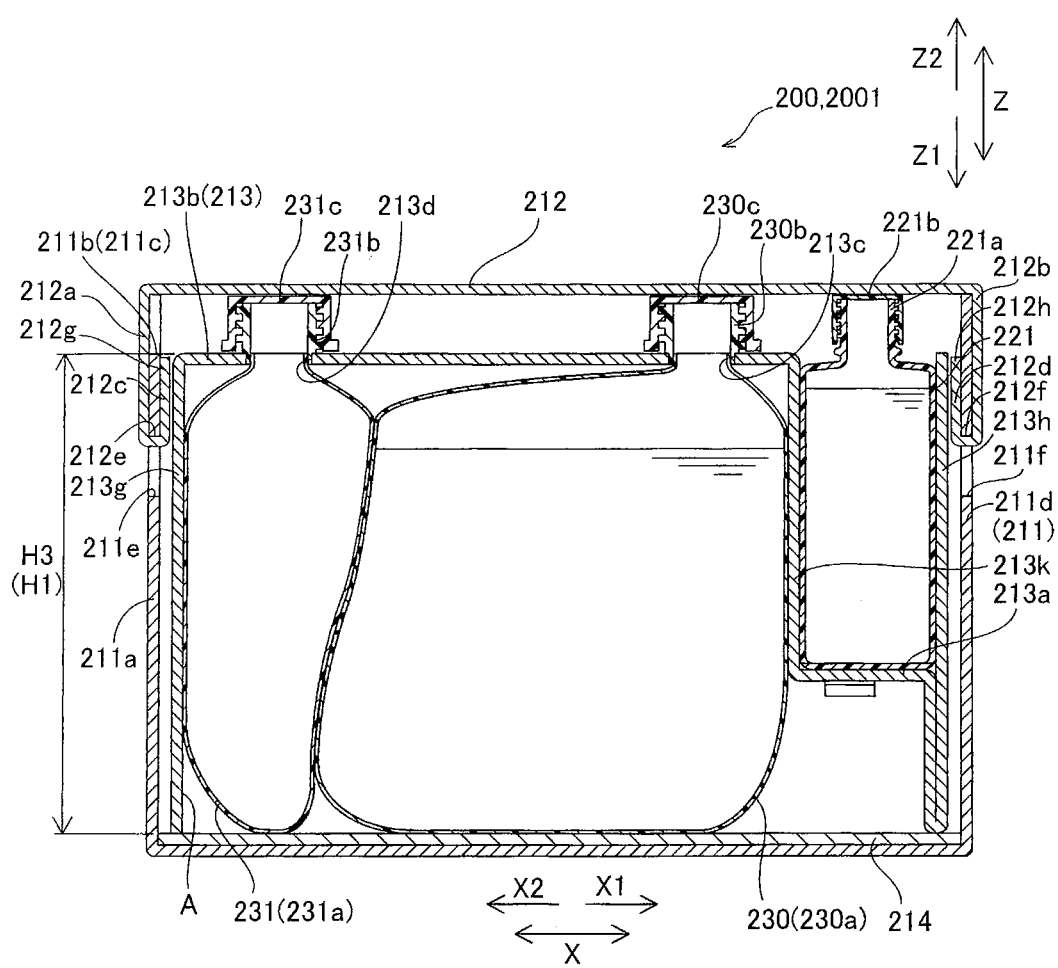
FIG. 29 is a cross sectional view of the reagent set along the 2000-2000 line of FIG. 26 of the second embodiment of the present invention.
Figure 30:
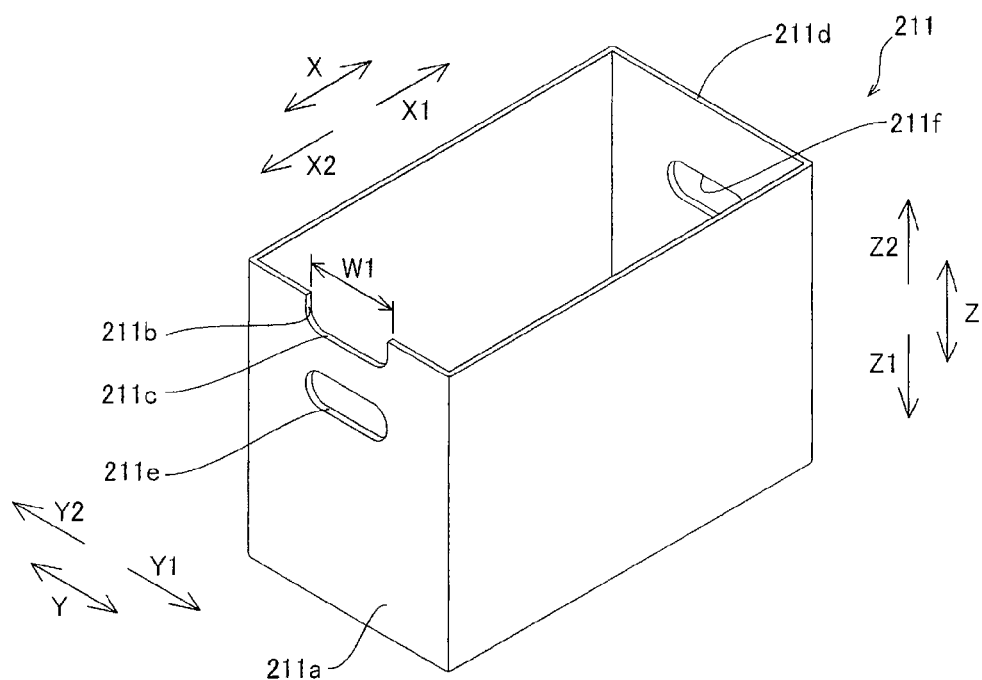
FIG. 30 is a perspective view showing the box body of the reagent set of the second embodiment of the present invention.

As shown in FIGS. 28 through 30, handles 211e and 2211f are respectively provided on the side surface 211a on the side in the arrow X2 direction of the box body 211, and side surface 211d on the side in the arrow X1 direction. As shown in FIG. 31, the handle 211e is formed by cutting out a rectangular shape slot extending in the Y direction below (side in the arrow Z1 direction) of the notch 211b on the side surface 211a on the side in the arrow 2 direction of the box body 211. As shown in FIG. 30, the handle 211f is formed by cutting out a rectangular shaped slot extending in the Y direction at the same height position as the handle 211e.

As shown in FIGS. 28 and 29, the cover 212 is mounted so as to cover the side surface 211d on the side in the arrow X1 direction of the box body 211, and the side surface 211a on the side in the arrow X2 direction of the box body 211 that is provided with the notch 211b by mounting the cover 212 on the box body 211 so as to cover the box body 211 from the top (side in the arrow Z2 direction). Retainers 212c and 212d are respectively provided at the center of the bottom end of the side surface 212a on the side in the arrow X2 direction, and the center of the bottom end of the side surface 212b on the side in the arrow X1 direction of the cover 212. The retainers 212c and 212d are configured to engage the handles 211e and 211f, respectively, when the cover 212 is mounted so as to cover the top surface of the box body 211. The retainers 212c and 212d also have stoppers 212e and 212f that respectively abut the top of the handles 211e and 211f.

As shown in FIG. 29, the retainers 212c and 212d are respectively folded when the cover is mounted on the box body 211 so as to cover the top surface of the box body 211. Thus, the stoppers 212e and 212f abut the top of the handles 211e and 211f, and the leading end 212g of the retainer 212c and the leading end 212h of the retainer 212d lock to the inner sides of the box body 211 on the side surface 211a on the side in the arrow X2 direction of the box body 211 and the side surface 211d on the side in the arrow X1 direction of the box body 211. As a result, the retainer 212c is locked to handle 211e and the side surface 211a on the side in the arrow X2 direction of the box body 211, and the retainer 212d is locked to the handle 211f and the side surface 211d on the side in the arrow X1 direction of the box body 211.

The bottom end of the side surface 212a on the side in the arrow X2 direction of the cover 212 and the bottom end of the side surface 212b on the side in the arrow X1 direction of the cover 212 are respectively positioned at the same height as the tops of the handles 211e and 211f. Thus, since the user can easily grasp the handles 211e and 211f by hand (not shown in the drawing), it is possible to prevent difficulty for the user carrying the reagent set 200 (refer to FIGS. 26 and 28) caused by the side surfaces 213g and 213h (described later) blocking the slots of the handles 211e and 211f from the inside of the box body 211.

Figure 33:
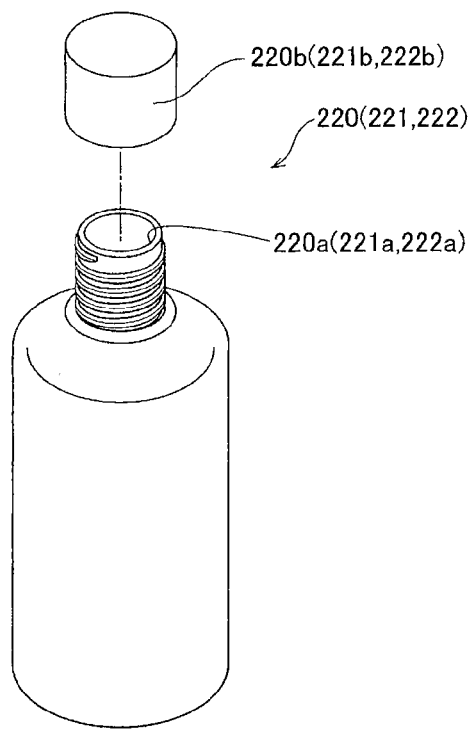
FIG. 33 is a perspective view showing the hemolytic agent container and staining agent container of the reagent set of the second embodiment of the present invention.

As shown in FIG. 33, the hemolytic agent storage containers 120 and 121, and staining agent storage container 122 include openings 220a, 221a, 222a for extracting the reagent contained therein, and caps 220b, 221b, 222b which screw onto the openings 220a, 221a, 222a, respectively.

Figure 34:
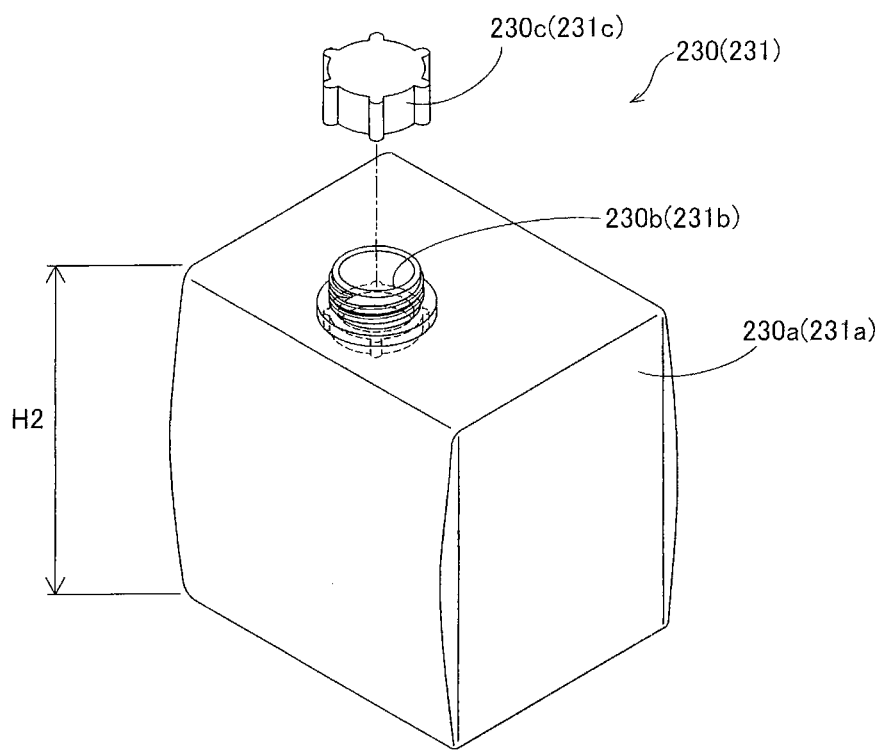
FIG. 34 is a perspective view showing the diluting liquid container and waste fluid container of the reagent set of the second embodiment of the present invention.

In the second embodiment, as shown in FIG. 34, the diluting liquid container 230 has a body 230a for accommodating the diluting liquid, and an opening 230b. The waste fluid container 231 is a container identical to the diluting liquid container 230, and has a body 231a for accommodating waste fluid, and an opening 231b.

The body 230a of the diluting liquid container 230 and the body 231a of the waste fluid container 231 are configured of flexible plastic. Thus, the body 230a of the diluting liquid container 230 is deformable according to the volume of diluting liquid accommodated therein, and the body 231a of the waste fluid container 231 is deformable according to the volume of waste fluid collected therein. The body 230a of the diluting liquid container 230 and the body 231a of the waste fluid container 231 are so-called gazette bags that have a match 230d (231d). Thus, the body 230a of the diluting liquid container 230 and the body 231a of the waste fluid container 231 respectively have a certain degree of independence. In this case, the body 230a of the diluting liquid container 230 and the body 231a of the waste fluid container 231 respectively have a height H2.

Figure 35:
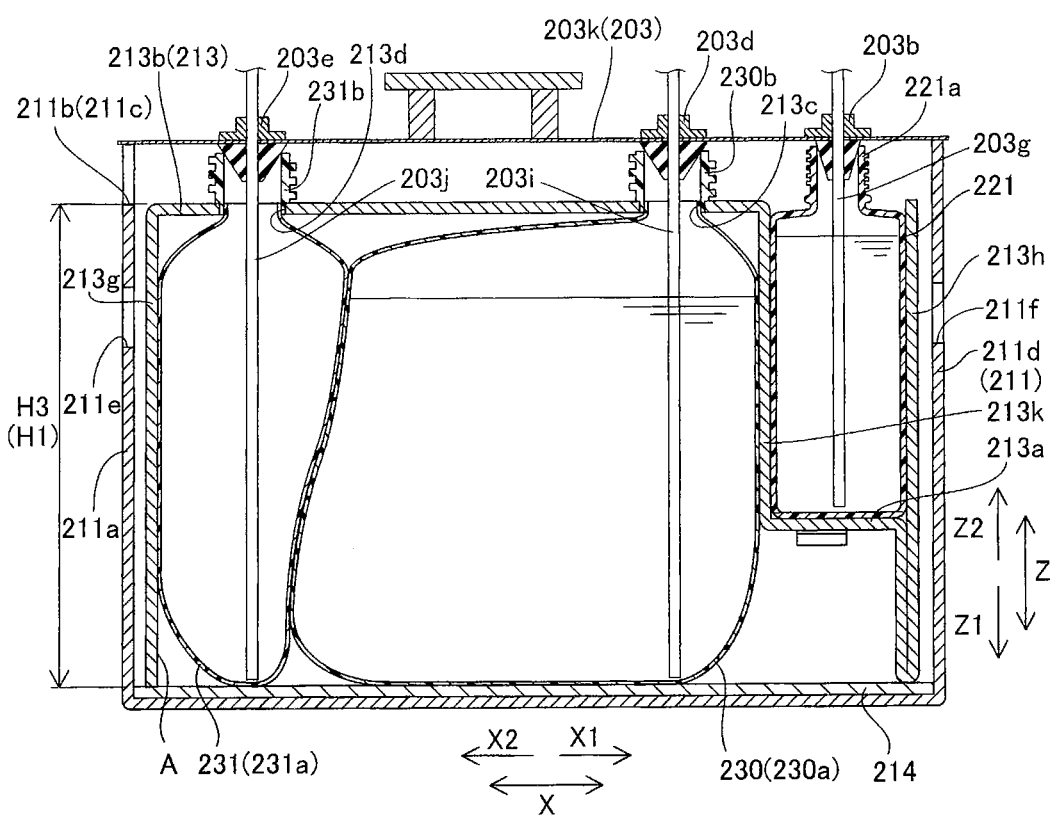
FIG. 35 is a cross sectional view of the unused reagent set along the 2000-2000 line of FIG. 25 of the second embodiment of the present invention.

As shown in FIGS. 27 and 35, the opening 230b of the diluting liquid container 230 and the opening 231b of the waste fluid container 231 are position on the top of the box body 211, and the center in the Y direction of the box body 211, respectively. As shown in FIG. 35, the reagent extraction unit 203d (reagent aspirating tube 203i) and waste fluid discharging unit 203e (waste fluid discharging tube 203j) are inserted in the openings 203b and 231b, respectively. As shown in FIG. 32, the opening 231b of the waste fluid container 231 has a width W2 in the Y direction.

As shown in FIGS. 27 and 35, the opening 231b of the waste fluid container 231 is disposed near the side surface 211a on the side in the arrow X2 direction of the box body 211, and is positioned opposite the notch forming 211b in the X direction.

Figure 36:
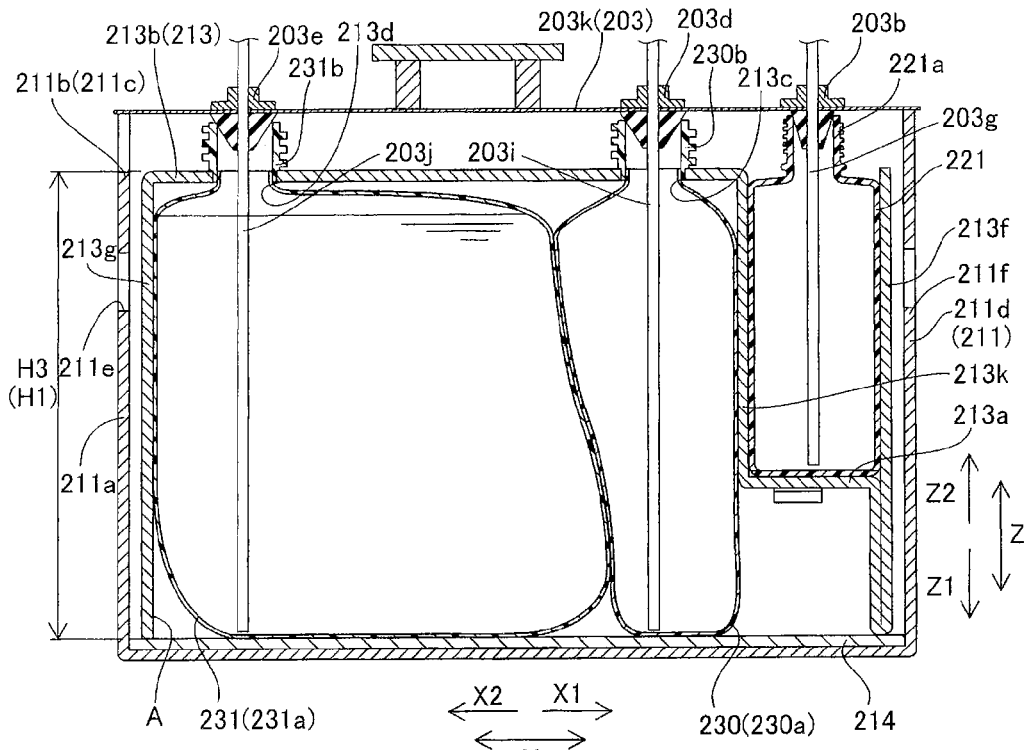
FIG. 36 is a cross sectional view of the used reagent set along the 2000-2000 line of FIG. 25 of the second embodiment of the present invention.

As shown in FIG. 35, prior to use of the reagent set 200, the approximately 4 liters of diluting liquid is accommodated as a reagent in the diluting liquid container 230, and nothing is accommodated in the waste fluid container 231. However, as shown in FIG. 36, after use of the reagent set 200, there is scant diluting liquid accommodated in the diluting liquid container 230, and the waste fluid container 231 accommodates less than 5 liters of waste fluid including the reagents from the hemolytic agent storage container 220, 221, and staining agent storage container 222, and the diluting liquid from the diluting liquid container 230. In this case, it is possible to prevent waste fluid from overflowing from the waste fluid container 231 caused by collecting more than 5 liters of waste fluid in the waste fluid container 231 by accommodating approximately 4 liters of diluting liquid in the diluting liquid container 230 that is capable of accommodating approximately 5 liters of fluid.

As shown in FIGS. 28 and 34, before and after use of the reagent set 200, the caps 230c and 231c are screwed on the openings 230b and 231b, respectively.

As shown in FIGS. 28 and 29, the interior member 213 of the container 210 is anchored and held within the box body 211. The top (side in the arrow Z2 direction) of the interior member 213 has a first support surface 213a provided on the side in the X1 direction, and a second support surface 213b provided on the side in the arrow X2 direction above (side in the arrow Z2 direction) the first support surface 213a. As shown in FIG. 28, the hemolytic agent storage containers 220, 221, and staining agent storage container 222 are arranged in a row sequentially from the side on the arrow Y1 direction on the first support surface 213a. Thus, as shown in FIG. 29, the bottom surfaces (surfaces on the side in the arrow Z1 direction) of the hemolytic agent storage containers 2220, 221, and staining agent storage container 222 are positioned on the side above the bottom surfaces of the diluting liquid container 230 and waste fluid container 231. As shown in FIG. 27, the openings 220a, 221a, and 222a of the hemolytic agent storage containers 220, 221, and staining agent storage container 222 are positioned below the top end of the box body 211 with the hemolytic agent storage containers 220 and 221, and the staining agent storage container 222 disposed on the top surface of the first support surface 213a (refer to FIG. 35).

In the second embodiment, as shown in FIGS. 28 and 35, the second support surface 213b is a flat surface perpendicular to the Z direction and has a height H3 (refer to FIG. 35) in the Z direction. The height H3 of the second support surface 213b is identical to the height H1 of the bottom 211c of the notch 211b. That is, the second support surface 213b of the interior member 213 and the bottom 211c of the notch 211b form a plane.

Figure 37:
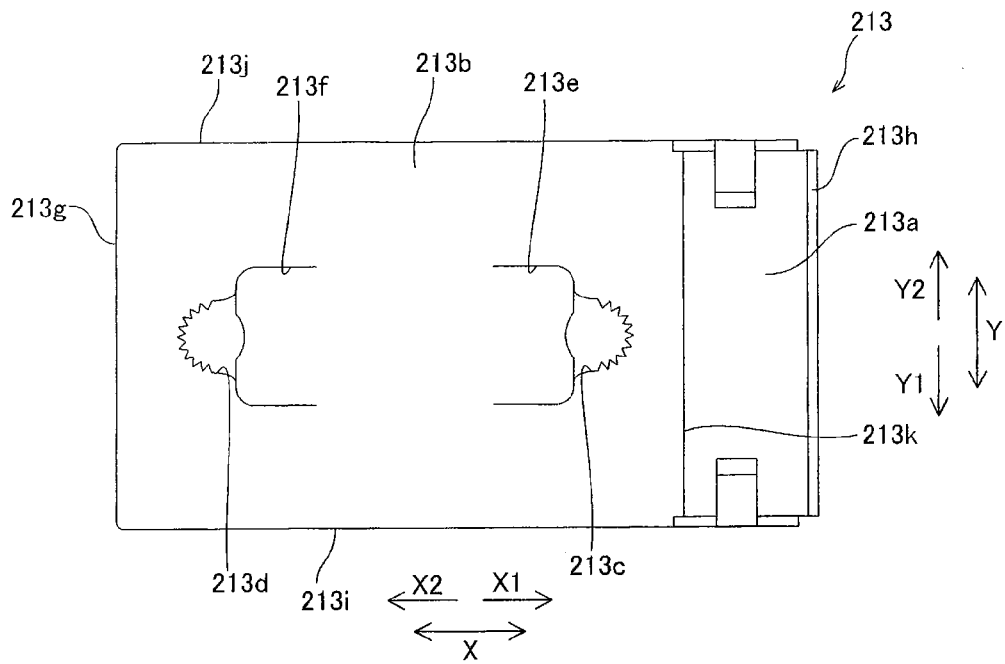
FIG. 37 is a top view showing the interior member of the reagent set of the second embodiment of the present invention.

As shown in FIG. 37, the second support surface 213b is provided with a support 213c formed on the side in the arrow X1 direction, and a support 213d formed on the side in the arrow X2 direction. As shown in FIG. 35, the opening 230b of the diluting liquid container 230 is latched to the support 213c with the bottom end (top end of the body 230a) of the diluting liquid container 230 inserted in the support 213c. The opening 213b of the waste fluid container 231 is also latched to the support 213d with the bottom end (top end of the body 231a) of the opening 231b of the waste fluid container 231 inserted in the support 213d. Thus, the diluting liquid container 230 and the waste fluid container 231 are supported by the second support surface 213b with the openings 230b and 231b exposed above the second support surface 213b.

As shown in FIG. 35, the diluting liquid container 230 is supported by the support 213c of the second support surface 213b in the box body 211 with the opening 230b of the diluting liquid container 230 positioned on the side in the arrow X1 direction from the center of the body 230a. As shown in FIG. 36, the waste fluid container 231 is supported by the support 213d of the second support surface 213b in the box body 211 with the opening 231b of the waste fluid container 231 positioned on the side in the arrow X2 direction from the center of the body 230a.

As shown in FIGS. 35 and 36, the height H3 of the second support surface 213b is slightly greater than the height H2 (refer to FIG. 34) of the body 231a of the waste fluid container 231 and the body 230a of the diluting agent container 230. Thus, the diluting liquid container 230 and waste fluid container 231 are supported in a suspended state by the supports 213c and 213d with the body 230a of the diluting liquid container 230 and the body 231a of the waste fluid container 231 in deformed states. As shown in FIG. 28, part of the bottom surface of the body 230a of the diluting liquid container 230 and part of the bottom surface of the body 231a of the waste fluid container 231 is anchored to the mat 214 disposed on the side in the arrow Z1 direction inside the box body 211 by adhesive tape not shown in the drawing. Thus, the diluting liquid container 230 and waste fluid container 231 can be respectively supported within the box body 211.

Figure 38:
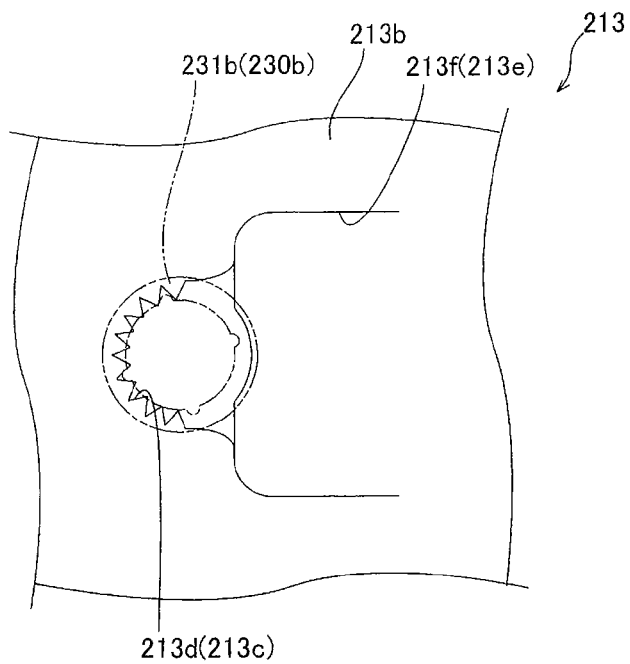
FIG. 38 is an enlarged top view showing the edge of the support part of the second support surface of the interior member of the reagent set of the second embodiment of the present invention.

As shown in FIGS. 37 and 38, the inner surface on the side in the arrow X1 direction of the support 213c and the inner surface on the side in the arrow X2 direction of the support 213d respectively have a plurality of concavoconvexities. As shown in FIG. 38, the outer surface of the opening 230b of the diluting liquid container 230 and the outer surface of the opening 231b of the waste fluid container 230 respectively have protrusions. Thus, the concavoconvexities of the supports 213c and 213d can be locked to the protrusions on the outer surface of the openings 230b and 231b. As a result, when a user (not shown in the drawing) removes the caps 230c and 231c (refer to FIG. 34) mounted on the openings 230b and 231b, respectively, it is possible to prevent difficulty in removing the caps 230c and 231c caused by movement of the diluting liquid container 230 and waste fluid container 231 via the rotation of the caps 230c and 231c.

As shown in FIG. 37, notches 213e and 213f are provided on the side in the arrow X2 direction of the support 213c and on the side in the arrow X1 direction of the support 213d, respectively. The side in the arrow X2 direction of the support 213c of the second support surface 213b is configured to be upwardly (side in the arrow Z2 direction in FIG. 28) deformable via the notch 213e, and the side in the arrow X1 direction of the support 213d of the second support surface 213b is configured to be upwardly deformable via the notch 213f. Thus, as shown in FIG. 28, the opening 230b of the diluting liquid container 230 is easily infixed on the support 213c by the upward deformation of the side in the arrow X2 direction of the support 213c when the user mounts the diluting liquid container 230 on the support 213c of the second support surface 213b from below (side in the arrow Z1 direction). Moreover, the opening 231b of the waste fluid container 231 is easily infixed on the support 213d by the upward deformation in the arrow X1 direction of the support 213d when the waste fluid container 231 is mounted on the support 213d of the second support surface 213b from below.

As shown in FIG. 37, side surfaces 213g and 213h are provided on the side in the arrow X2 direction and the side in the arrow X1 direction of the interior member 213 so as to be along the side surface 211a on the side in the arrow X2 direction and the side surface 211d on the side in the arrow X1 direction of the box body 211. As shown in FIG. 35, the side surfaces 213g and 213h are arranged so as to block the slot-like notched part of the handles 211e and 211f from inside the box body 211. Thus, it is possible to prevent the user (not shown in the drawing) from coming into contact with the reagents of the hemolytic agent storage containers 220, 221, staining agent storage container 222, diluting liquid of the diluting liquid container 230, and waste fluid of the waste fluid container 231 through the handles 211e and 211f. The side surface 213g is integratedly formed with the second support surface 213b on the side in the arrow X1 direction so that the height H3 of the top end of the side surface 213g is the same as the height H3 of the second support surface 213b.

As shown in FIG. 28, the body 230a of the diluting liquid container 230 and the body 231a of the waste fluid container 231 are disposed in a mutually adjacent state inside the interior region A (refer to FIG. 29) configured by the mat 214 and interior member 213. Specifically, the interior region A is configured by a region circumscribed by the side surface 213i on the side in the arrow Y1 direction of the interior member 213, side surface 213j on the side in the arrow Y2 direction of the interior member 213, side surface 213k disposed between the first support surface 213a and second support surface 213b positioned on the side in the arrow X1 direction of the interior member 213, side surface 213g on the side in the arrow X2 direction of the interior member 213, and mat 214. The diluting liquid container 230 and waste fluid container 231 are disposed in contact with the side surfaces 213i and 213j inside the interior region A.

In the second embodiment, the interior region A of the box body 211 to have a volume capacity approximately ¾ of the total volume capacity of the aggregate volume capacity of the body 230a of the fluid-filled diluting liquid container 230 and the capacity of the body 231a of the fluid-filled waste fluid container 231. As shown in FIG. 35, prior to use of the reagent set 200 (initial state), the occupied volume capacity of the waste fluid container 231 in the interior region A of the box body 211 is less than the occupied volume capacity of the diluting liquid container 230; and, as shown in FIG. 36, after use of the reagent set 200, the occupied volume capacity of the of the diluting liquid container 230 in the interior region A of the box body 211 is less than the occupied volume capacity of the waste fluid container 231. Note that the structure of the second embodiment is in other aspects identical to that of the first embodiment.

The sequence for using the reagent set 200 of the second embodiment of the present invention is described below with reference to FIGS. 25 through 29, 35, 36, and 39 through 41.

As shown in FIG. 26, prior to use of the reagent set 200, the cover 212 is first mounted on the box body 211 so as to cover the top surface of the box body 211. The waste fluid container 231 is also empty of waste fluid, as shown in FIG. 28.

Then, when the reagent set 200 is in use, the user (not shown in the drawing) removes the cover 212 mounted on the box body 211, and removes the caps 220b, 221b, 222b, 230c, and 231c respectively screwed on the openings, 220a, 221a, 222a, 230b, and 231b. As shown in FIGS. 25 and 25, the user arranges the reagent extraction member 293 so as to cover the box body 211 from above (side in the arrow Z2 direction). The reagent aspirating tubes 203g of the reagent extraction member 203 are inserted in the openings 220a, 221a, 222a, and the reagent aspirating tube 203i is inserted in the opening 230b, respectively. The waste fluid discharging tube 203j is also inserted in the opening 231b.

Figure 39:
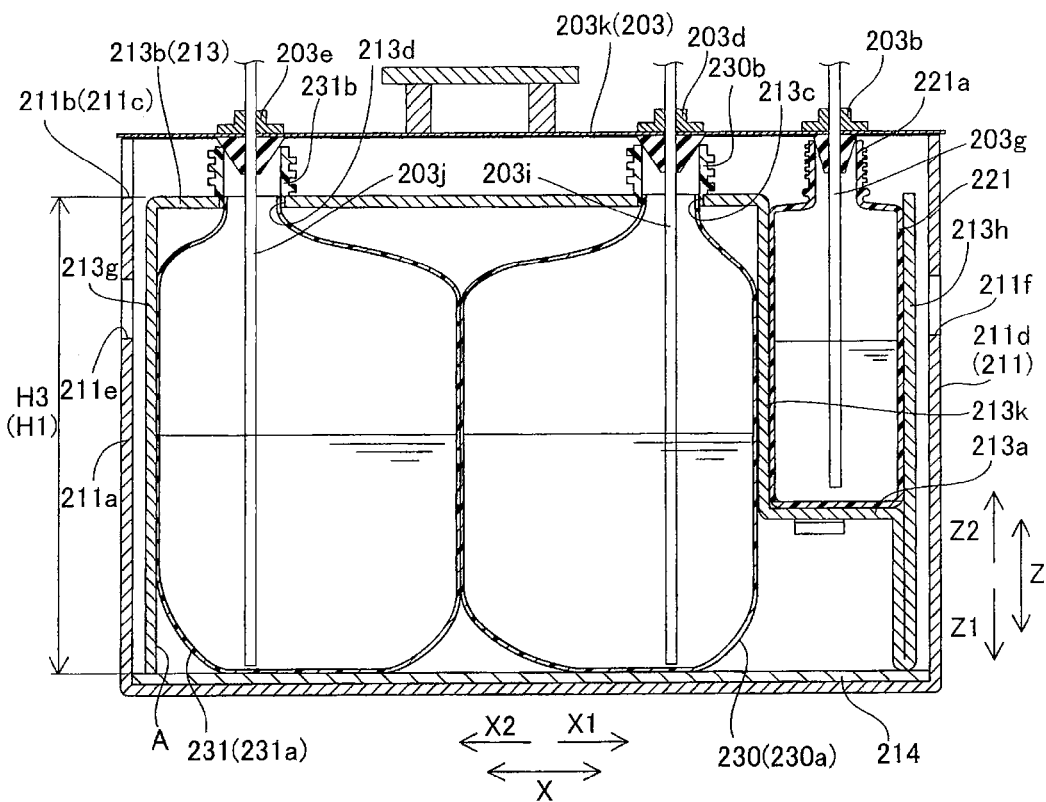
FIG. 39 is a cross sectional view of the reagent set during use along the 2000-2000 line of FIG. 25 of the second embodiment of the present invention.

When the user operates the sample analyzer 2, a sample (not shown in the drawing) is analyzed in the sample analyzer 2, and the ratio of the occupied volume capacity of the body 230a of the diluting liquid container 230 decreases in the interior region A due to the decrease in the diluting liquid accommodated in the body 230a of the diluting liquid container 230, as shown in FIG. 39. However, the ratio of the occupied volume capacity of the body 231a of the waste fluid container 231 increases in the interior region A due to the increase in the waste fluid collected in the body 231a of the waste fluid container 231. Thus, the decreased part of the occupied volume capacity in the body 230a of the diluting liquid container 230 occupies the body 231a of the waste fluid container 231 disposed adjacent to the body 230a of the diluting liquid container 230.

When the use of the reagent set 200 then ends, the amount of waste fluid collected in the body 231a of the waste fluid container 231 is equal to the total amount of reagents accommodated in the hemolytic agent storage containers 220, 221, staining agent storage container 222, and diluting liquid accommodated in the diluting liquid container 230, as shown in FIG. 36.

Thereafter, the screws the caps 220b, 221b, 222b, 230c, and 231c on the opening 220a of the hemolytic agent storage container 220, opening 221a of the hemolytic agent storage container 221, opening 222a of the staining agent storage container 222, opening 230b of the diluting liquid container 230, and opening 231b of the waste fluid container 231, respectively to seal the openings.

As shown in FIG. 26, the user then mounts the cover 212 on the box body 211 to cover the box body 211 from above. In this case, the cover 212 is mounted on the box body 211 so that the bottom end of the side surface 212a on the side in the arrow X2 direction of the cover 212 and the bottom end of the side surface 212b on the side in the arrow X1 direction of the cover 212 are respectively positioned at the same height as the tops of the handles 211e and 211f. Finally, the user folds the retainers 212c and 212d with the leading ends of the retainers 212c and 212d of the cover 212 inserted inside the box body 211 through the handles 211e and 211f (refer to FIG. 28). Thus, the retainer 212c is locked to handle 211e at the side surface 211a on the side in the arrow X2 direction of the box body 211, and the retainer 212d is locked to the handle 211f at the side surface 211d on the side in the arrow X1 direction of the box body 211, as shown in FIG. 29. Then, the used reagent set 200 is stored at a predetermined location.

Figure 40:
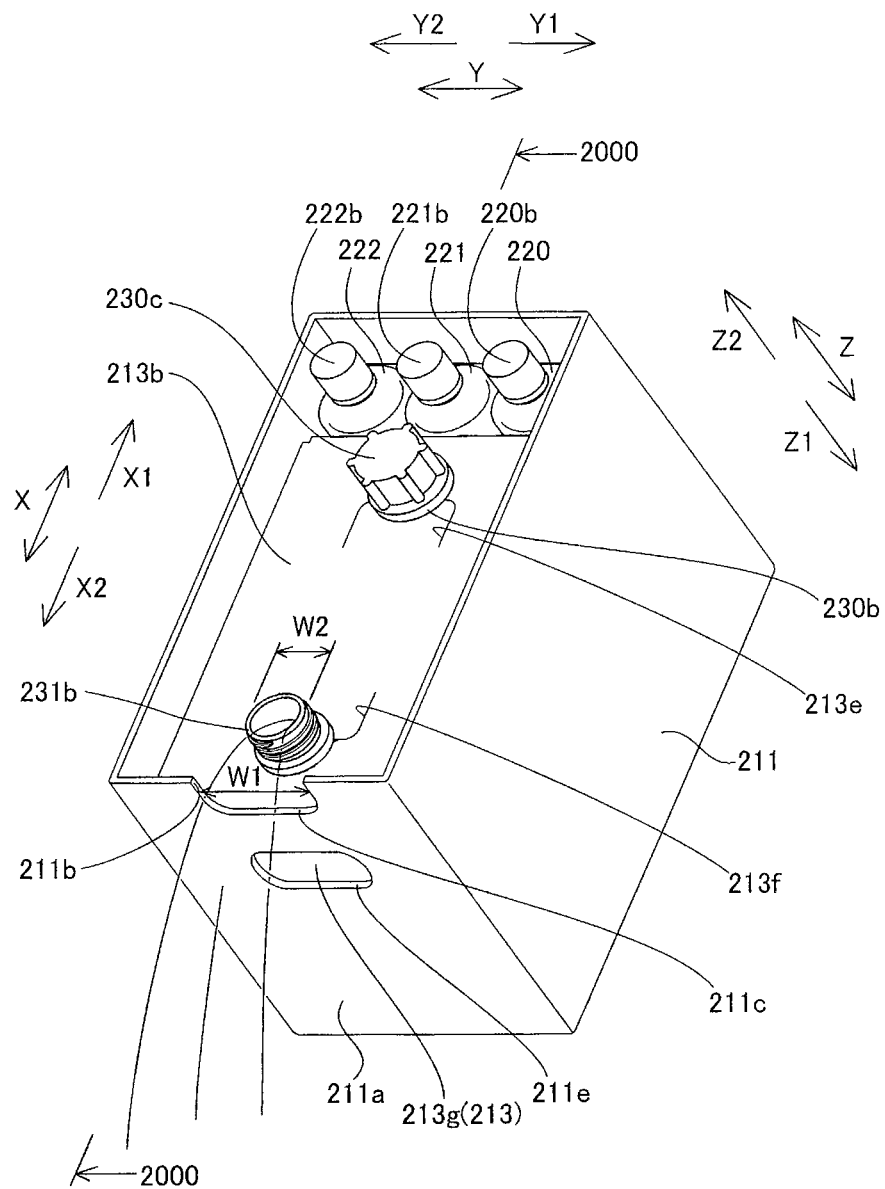
FIG. 40 is a perspective view illustrating the discharge of the waste fluid from the waste fluid container to the outside of the reagent set of the second embodiment of the present invention.
Figure 41:
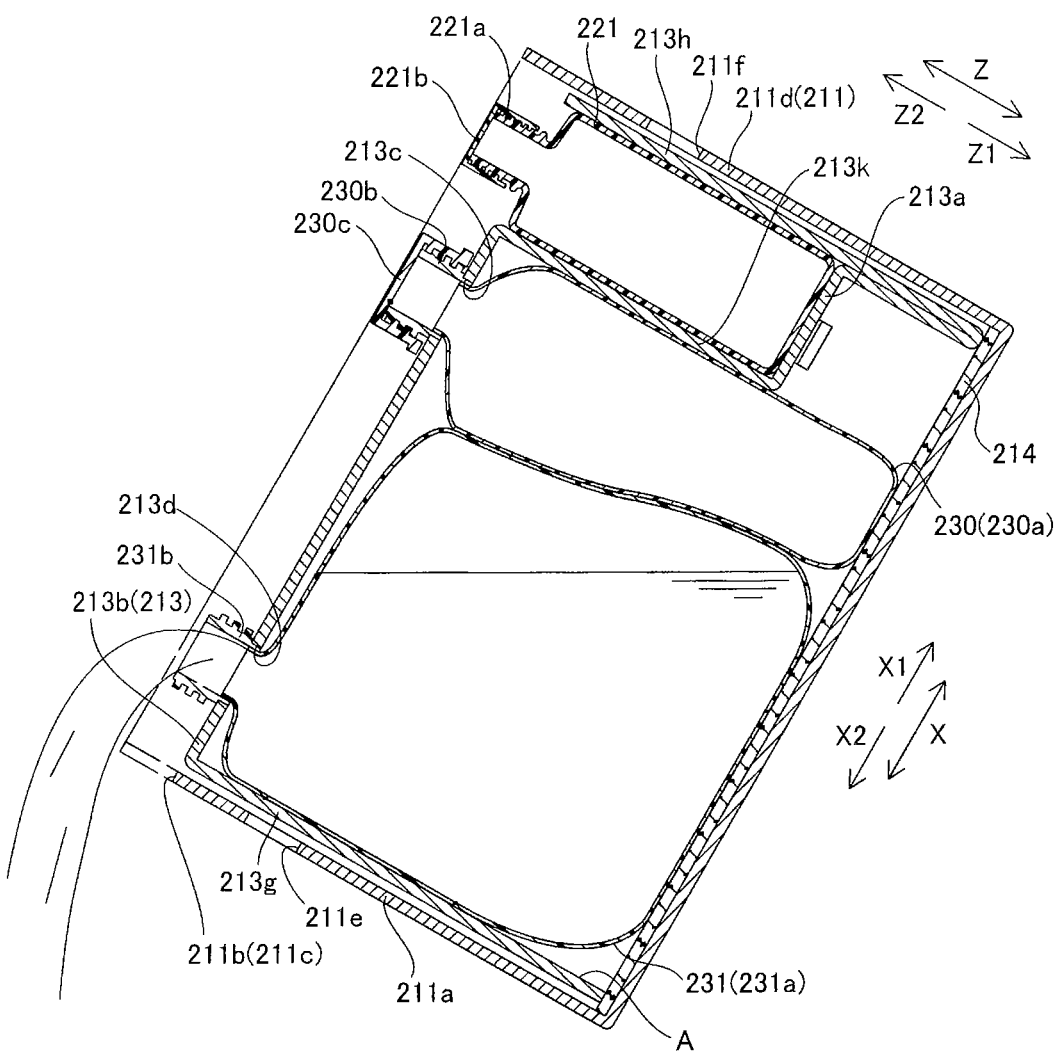
FIG. 41 is a cross sectional view along the 2000-2000 line of FIG. 40 illustrating the discharge of the waste fluid from the waste fluid container to the outside of the reagent set of the second embodiment of the present invention.

In the second embodiment, when the waste fluid collected in the waste fluid container 231 of the used reagent set 200 is disposed separately from the reagent set 200, the user removes the cover 212 mounted on the box body 211, and removes the cap 231c screwed onto the opening 231b. As shown in FIGS. 40 and 41, the user then inclines the reagent set 200 (container 210) in the X direction so that the side surface 212a on the side in the arrow X2 direction of the box body 211 is lower than the side surface 212b on the side in the arrow X1 direction. Thus, the waste fluid of the waste fluid container 231 is discharged toward the center direction of the side surface 211d on the side in the arrow X2 direction of the box body 211 and outside the box. In this case, the waste fluid of the waste fluid container 231 is discharged from the opening 231b of the waste fluid container 231 through a discharge path configured by the removed part of the notch 211b and above the notch 211b provided so as to overlap the entire region of the opening 231b of the waste fluid container 231 at the side surface 212a on the side in the arrow X2 direction of the box body 211. Note that the use sequence of the second embodiment is in other aspects identical to that of the first embodiment.

As described above in the second embodiment, the discharging waste fluid is prevented from adhering to the side surface 211*a* on the side in the arrow X2 direction of the box body 211 because the waste fluid discharged from the opening 231*b* of the waste fluid container 231 passes through the removed part of the notch 211*b* when the user inclines the reagent set 200 (container 210) in the X direction and discharges the waste fluid from the opening 231*b* of the waste fluid container 231 by disposing the opening 231*b* of the waste fluid container 231 near the side surface 211*a* on the side in the arrow X2 direction of the box body 211, that is, at a position in the X direction corresponding to the notch 211*b*. Thus, the waste fluid is prevented from adhering to the user.

As described above in the second embodiment, the user can easily discharge the waste fluid from the opening 231*b* of the waste fluid container 231 without the waste fluid adhering to the side surface 211*a* on the side in the arrow X2 direction of the box body 211 since the opening 231*b* is positioned in the center in the Y direction and at the top of the box body 211 by providing the notch 211*b* in the center in the Y direction of the top end of the side surface 211*a*.

As described above in the second embodiment, the waste fluid is prevented from adhering to the second support surface 213*b* when the waste fluid is discharged from the waste fluid container 231 because the second support surface 213*b* of the interior member 213 is not disposed on the waste fluid discharge path configured by the removed part of the notch 211*b* and above the notch 211*b* by configuring the second support surface 213*b* of the interior member 213 and the bottom 211*c* of the notch 211*b* as a plane.

As described above in the second embodiment, the diluting liquid container 230 and waste fluid container 231 are supported by the supports 213*c* and 213*d*, respectively, so as to respectively deform according to the volume of accommodated fluid while being maintained in a mutually adjacent state by a configuration in which the diluting liquid container 230 and waste fluid container 231 are respectively supported by the supports 213*c* and 213*d* of the interior member 213 in a mutually adjacent state, and the body 230*a* of the diluting liquid container 230 and the body 231*a* of the waste fluid container 231 are configured of a flexible plastic that is deformable according to the volume of accommodated fluid (diluting liquid and waste fluid).

As described above in the second embodiment, the interior region A of the box body 211 is configured to have a volume capacity approximately ¾ of the total volume capacity of the aggregate volume capacity of the fluid-filled diluting liquid container 230 and the fluid-filled waste fluid container 231; prior to use of the reagent set 200 (initial state), the occupied volume of the waste fluid container 231 in the interior region A of the box body 211 is less than the occupied volume of the diluting liquid container 230, and the decreased part of the occupied volume in the body 230*a* of the diluting liquid container 230 caused by analysis of samples in the sample analyzer 2 is received in the body 231*a* of the waste fluid container 231 disposed adjacent to the body 230*a* of the diluting fluid container 230, such that it is unnecessary to ensure the interior region A of the box body 211 is of sufficient total volume for the volume when the diluting liquid fills the diluting liquid container 230 and the volume when the waste fluid fills the waste fluid container 231 in order to accommodate the diluting liquid container 230 and waste fluid container 231. Thus, enlargement of the reagent set 200 is prevented.

As described above in the second embodiment, the bottom surface of the diluting liquid container 230 and the bottom surface of the waste fluid container 231, which are flexible and deformable according to the volume of accommodated fluid (diluting liquid and waste fluid), can be prevented from spreading due to its own weight and the weight of the accommodated fluid because the diluting liquid container 230 and waste fluid container 231 are supported in suspended states by the supports 213*c* and 213*d* with the body 230*a* of the diluting liquid container 230 and the body 231*a* of the waste fluid container 231 in deformed states. Specifically, it is possible to prevent the problem of not completely using all of the diluting liquid of the diluting liquid container 230 caused spreading of the bottom surface of the diluting liquid container 230.

As described above in the second embodiment, the cover 212 is prevented from being removed from the box body 211 even when the reagent set 200 is mistakenly dropped when being carried with the cover 212 covering the notch 211*b* of the box body 211 because the cover 212 can be latched to the side surfaces 211*a* and 211*d* of the box body 211 by providing the retainers 212*c* and 212*d* to latch to the handles 211*e* and 211*f* when the cover 212 is mounted on the box body 211 so as to cover the top surface of the box body 211 by mounting on the center of the bottom end of the side surface 212*a* on the side in the arrow X2 direction of the cover 212. Thus, it is possible to prevent reagent, diluting liquid, and waste fluid from adhering to the user caused by the removal of the cover 212 from the box body 211.

As described above in the second embodiment, separate designs of the diluting liquid container 230 and waste fluid container 231 are unnecessary since the diluting liquid container 230 and the waste fluid container 231 are identical containers.

As described above in the second embodiment, the diluting liquid container 230, hemolytic agent storage containers 220 and 221, and staining agent storage container 222 are arranged so that the height of the top end of the diluting liquid container 230, hemolytic agent storage containers 220 and 221, and staining agent storage container 222 are the same even when the diluting liquid container 230, hemolytic agent storage containers 220, 221, and staining agent storage container 222 have different volume capacities due to the different amount of diluting liquid used, amounts of hemolytic agent used, and amount of staining agent used in the sample analyzer 2 by positioning the bottom surfaces of the hemolytic agent storage containers 220, 221, and staining agent storage container 222 higher than the bottom surface of the diluting liquid container 230 and waste fluid container 231.

As described above in the second embodiment, separate designs of the hemolytic agent storage containers 220, 221 and staining agent storage container 222 are unnecessary because the hemolytic agent storage containers 220, 221, and staining agent storage container 222 have the same shape and can accommodate approximately 250 mm of fluid. Note that the effectiveness of the second embodiment is in other aspects identical to that of the first embodiment.

Note that the embodiments of the present disclosure are in all respects examples and are not to be considered as limiting in any way. The scope of the present invention is defined solely by the appended claims, is not affected to any degree by the statements within this summary, and includes all modifications which fall within the meanings and equivalences of the scope of the claims.

For example, although reagent set 100 (200) of the first and second embodiments are described by way of examples in which four types of reagents (hemoglobin measurement reagent, white blood cell classification and measurement reagent, reticulocyte measurement reagent, diluting liquid) are accommodated in the hemolytic agent storage container 120 (220), hemolytic agent storage container 121 (221), staining agent storage container 122 (222), and diluting liquid container 130 (230), the present invention is not limited to these examples. The reagent accommodated in the reagent containers in the reagent set is not limited to four types in the present invention. That is, one type of reagent alone may be accommodated in the reagent storage container, or more than four types of reagent may be accommodated in the reagent containers in the reagent set. A plurality of reagents may also be mixed and accommodated in a single reagent storage container in the reagent set.

Although the first and second embodiments have been described by way of examples in which an opening 131e (231b) is provided at only one location on the waste fluid container 131 (231), the present invention is not limited to these examples. The present invention may also be configured to separately provide the waste fluid container with an opening for collection and a discharge opening.

Although the first embodiment is described by way of example in which the container holding member 113 is held and anchored inside the box body 111 in the Y direction by sufficiently reducing the gap in the Y direction between the box body 111 and the container holding member 113, the present invention is not limited to this example. Other configurations may be used in the present invention insofar as the container holding member is anchored and held inside the box. For example, the container holding member may also be anchored and held by adhering the member inside the box.

Although the first and second embodiments are described by way of examples in which the opening 130e (230b) of the diluting liquid container 130 (230) and the opening 131e (231b) of the waste fluid container 131 (231) are disposed at predetermined positions, the present invention is not limited to these examples. Other configurations may also be used in the present invention insofar as the openings are disposed at predetermined positions. For example, the openings may be disposed at the predetermined positions by adhering and anchoring the diluting liquid container and waste fluid container to the container holding member.

Although the first embodiment is described by way of example in which the side surface 113c is formed as a rectangular equilateral triangle with the apex positioned downward and the bottom position upward by beveling both corners in the X direction, that is, below the side surface 113c on the side in the arrow Y1 direction, and forming the corners on the side in the arrow Y1 direction in a curved shape by beveling below (side in the arrow Z1 direction) the pair of side surfaces 113b, the present invention is not limited to this example. The present invention is not limited to a curved shape, or rectangular equilateral triangle shape insofar as at least one corner on the bottom side of the side surface is beveled.

Although the first embodiment is described by way of example in which a blue identification marker 113j, green identification marker 113k, and red identification marker 113l (second identification markers) are formed on the edge on the side in the arrow X1 direction of the top surface 113a, the present invention is not limited to this example. The second identification markers also may be formed on part of the container holding member other than the edge ion the side in the arrow X1 direction of the top surface insofar as the second identification markers correspond to the positions of the hemolytic agent storage containers and staining agent storage container. The second identification markers also may be formed at positions on the side surface on the side in the arrow X1 direction of the box corresponding to the positions of the hemolytic agent storage containers and staining agent storage container rather than on the container holding member.

Although the second embodiment is described by way of example in which the notch 211b of the box body 211 is provided at the center top end of the side surface 211a to occupy approximately half the top of the side surface 211a on the side in the arrow X2 direction of the box body 211, the present invention is not limited to this example inasmuch as the notch also may be formed to occupy the entire top end of the side surface of the box body. The notch also may be provided in the center of the side surface of the box body insofar as the notch is provided in a part near and opposite the opening of the waste fluid container.

Although the second embodiment is described by way of example in which the second support surface 213b of the interior member 213 and the bottom 211c of the notch 211b form a plane, the present invention is not limited to this example inasmuch as the height H3 of the second support surface of the interior member may be less than the height H1 of the bottom of the notch. Since the effectiveness of the present invention can be obtained if part of the second support surface of the interior member, which is positioned between the notch and the opening of the waste fluid container, is lower than the height H1 of the bottom of the notch, the part of the second support surface of the interior member that is not positioned between the notch and the opening of the waste fluid container may be higher than the height H1 of the base of the notch.

Although the second embodiment is described by way of example in which the amount of reagent accommodated in the hemolytic agent storage container 220, hemolytic agent storage container 221, staining agent storage container 222, and diluting liquid accommodated in the diluting liquid container 230 is the same amount as the amount of waste fluid collected in the body 231a of the waste fluid container 231, the present invention is not limited to this example inasmuch as the waste fluid collected in the waste fluid container also may include reagent used in the sample analyzer received from a container not included in the reagent set. In this case, the amount of waste fluid collected in the waste fluid container must not exceed the capacity (approximately 5 liters) of the waste fluid container.

Although the first and second embodiments are described by way of examples in which the waste fluid container 131 (231) is identical to the diluting liquid container 130 (230), the present invention is not limited to these examples inasmuch as the waste fluid container need not be identical to the diluting liquid container.

Although the first and second embodiments are described by way of examples in which the hemolytic agent storage container 120 (220), hemolytic agent storage container 121 (221), and staining agent storage container 122 (222) have the same shape and same volume capacity of approximately 250 mm, the present invention is not limited to these examples inasmuch as the hemolytic agent storage containers, and staining agent storage container need not have the same shape and volume capacity.

What is claimed is:

1. A reagent container set comprising:
a first reagent container for accommodating a first reagent to be used in a sample analyzer, the top part of the first reagent container having a first aspiration opening for inserting a first reagent aspirating tube to aspirate the first reagent;
a waste fluid container for accommodating the first reagent used in the sample analyzer as a waste fluid, the top of the waste fluid container having a discharge opening for inserting a waste fluid discharging tube to discharge the waste fluid into the waste fluid container;

a box for accommodating the first reagent container and the waste fluid container;

a container holding member for holding the first reagent container and the waste fluid container so that the first aspiration opening and the discharge opening are disposed at predetermined positions, the container holding member being maintained at a predetermined position within the box;

a second reagent container to accommodate a second reagent to be used in the sample analyzer, the top part of the second reagent container having a second aspiration opening for inserting a second aspirating tube to aspirate the second reagent, and the height of the second reagent container being shorter than that of the first reagent container; and a container support for supporting the bottom of the second reagent container so that the bottom of the second reagent container is accommodated by the box at a position higher than the bottom of the first reagent container.

2. The reagent container set of claim 1, wherein the container holding member has a top surface part for holding the first reagent container and the waste fluid container, and side surface parts extending downward from the edge of the top surface part; and a bottom corner of at least one of the side surface parts is beveled.

3. The reagent container set of claim 2, wherein a bottom corner of at least one of the side surface parts is curved.

4. The reagent container set of claim 1, wherein the waste fluid container comprises:

a property of flexibility; and a cover for sealing the discharge opening, the discharge opening being sealed by the cover with gas entrapped within the interior of the waste fluid container prior to use.

5. The reagent container set of claim 1, wherein the container support is disposed between the box and the first reagent container.

6. The reagent container set of claim 5, further comprising a waste fluid container comprising:

a property of flexibility; and a cover for sealing the discharge opening, the discharge opening being sealed by the cover with gas entrapped within the interior of the waste fluid container prior to use, wherein the first reagent container is disposed between the container support and the waste fluid container.

7. The reagent container set of claim 1, wherein the box further comprises:

a box body having an opening on top; and a cover connected to the box body for closing the opening of the box body; and an opening maintainer for maintaining the opening of the box body in an open state.

8. The reagent container set of claim 1, wherein the top of the side surface of the box comprises a notch forming part for forming a notch through which passes the waste fluid discharged from the waste fluid container.

9. The reagent container set of claim 1, wherein the first aspiration opening is disposed on a first protrusion protruding from the top of the first reagent container; and the container holding member comprises a first holding hole for holding the first aspiration opening at a predetermined position by holding the first protrusion.

10. The reagent container set of claim 1, wherein the discharge opening is disposed on a second protrusion protruding from the top of the waste fluid container; and the container holding member comprises a second holding hole for holding the discharge opening at a predetermined position by holding the second protrusion.

11. The reagent container set of claim 1, wherein the box and the container holding member are formed by corrugated cardboard.

12. The reagent container set of claim 1, wherein the first reagent container and the waste fluid container are configured with the same volume capacity.

13. The reagent container set of claim 1, wherein the sample analyzer is a blood cell counting apparatus; and the first reagent container accommodates a dilution liquid as the first reagent.

14. The reagent container of claim 1, wherein the first reagent aspirating tube and the waste fluid discharging tube are supported by a common tube anchoring member.

15. A reagent set comprising:

the reagent container set of claim 1;

the first reagent accommodated in the first reagent container; and the second reagent accommodated in the second reagent container.

16. A reagent container set comprising:

a first reagent container for accommodating a first reagent to be used in a sample analyzer, the top part of the first reagent container having a first aspiration opening for inserting a first reagent aspirating tube to aspirate the first reagent;

a second reagent container for accommodating a second reagent to be used in the sample analyzer, the top part of the second reagent container having a second aspiration opening for inserting a second reagent aspirating tube to aspirate the second reagent, and the height of the second reagent container being shorter than that of the first reagent container;

a waste fluid container for accommodating the first reagent and the second reagent used in the sample analyzer as a waste fluid, the top of the waste fluid container having a discharge opening for inserting a waste fluid discharging tube to discharge the waste fluid;

a container support for supporting the bottom of the second reagent container so that the bottom of the second reagent container is positioned at a higher position than the bottom of the first reagent container, and so that the openings of the first reagent container and the second container are at the same position in height; and a box for accommodating the first reagent container, second reagent container, waste fluid container, and container support.

17. The reagent container set of claim 16, wherein the first reagent container and the waste fluid container have the same height.

18. The reagent container set of claim 16, further comprising a third reagent container for accommodating a third reagent to be used in the sample analyzer, wherein:

the third reagent container comprises a third aspiration opening disposed at the top of the container for inserting a third reagent aspirating tube to aspirate the third reagent;

the height of the third reagent container is the same as the height of the second reagent container; and the third reagent container is supported by the container support.

19. The reagent container set of claim 16, wherein the first reagent container, second reagent container, and waste fluid container are accommodated in the box so that the first aspiration opening, second aspiration opening, and discharge opening are disposed at the same height.

20. The reagent container set of claim 16, wherein the waste fluid container comprises:
   a property of flexibility; and
   a cover for sealing the discharge opening, the discharge opening being sealed by the cover with gas entrapped within the interior of the waste fluid container prior to use,
   wherein the first reagent container is disposed between the container support and the waste fluid container.

21. A reagent container set comprising:
   a box body defining a first region inside thereof, wherein the box body comprises a cover holding device configured to keep a cover open, the cover holding device being an ear attached to the box body and dimensioned to increase its size thereacross from shorter than a distance between the two tabs to larger than the distance therebetween, the ear being trapped between the two tabs to keep the cover open;
   a first interior member placed in the box body to define a second region within the first region, the second region being no larger than the first region;
   a first and a second containers, in which a reagent and a reagent waste are storable respectively, configured to collectively substantially occupy the second region and generally immobilized in the second region, each container having a generally tubular opening in a top surface thereof; and
   two holding devices provided in the first interior member so as to be spaced apart at a distance between the tubular openings of the first and second containers and configured to generally hold the tubular openings relative to each other and to the box body.

22. The reagent container set of claim 21, wherein the ear is a part of the box body and bent away from the box body.

23. The reagent container set of claim 21, wherein the first interior member comprises a top surface at least partially fit in the box body at a height not higher than a height of the box body.

24. The reagent container set of claim 23, wherein the first interior member further comprises a front surface rotatably extending from the top surface, the front surface being placed in the box body to reach at a bottom of the box body to define the height at which the top surface is situated in the box body.

25. The reagent container set of claim 23, wherein the first interior member further comprises a pair of side surface each rotatably extending from the top surface and generally in a shape of a fan.

26. The reagent container set of claim 23, wherein the first interior member further comprises a rear surface rotatably extending from the top surface and generally in a triangular shape becoming narrower as going away from the top surface.

27. The reagent container set of claim 23, wherein the two holding devices provided in the first interior member are holes formed in the first interior member, through which the tubular openings of the first and second containers are inserted.

28. The reagent container set of claim 21, wherein the box body has a removable notch located adjacent to the tubular opening of the second container.

29. The reagent container set of claim 21, further comprising a reagent extraction member placeable over the opened box body, the reagent extraction member is fixed with connectors arranged in a same geometry as an arrangement of the tubular openings of the first and second containers and the at least one third container.

* * * * *